United States Patent
Kitani et al.

(10) Patent No.: US 7,976,532 B2
(45) Date of Patent: Jul. 12, 2011

(54) MALE LUER CONNECTOR

(75) Inventors: Ichiro Kitani, Fukuroi (JP); Shigeaki Funamura, Fukuroi (JP); Kazuhiro Abe, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 408 days.

(21) Appl. No.: 12/159,545

(22) PCT Filed: Dec. 27, 2006

(86) PCT No.: PCT/EP2006/012546
§ 371 (c)(1),
(2), (4) Date: Jun. 27, 2008

(87) PCT Pub. No.: WO2007/073939
PCT Pub. Date: Jul. 5, 2007

(65) Prior Publication Data
US 2008/0300542 A1 Dec. 4, 2008

(30) Foreign Application Priority Data
Dec. 28, 2005 (JP) .................. 2005-378803

(51) Int. Cl.
*A61M 25/16* (2006.01)

(52) U.S. Cl. ...................... 604/533; 604/905

(58) Field of Classification Search .......... 604/240, 604/523, 533, 905
See application file for complete search history.

(56) References Cited

U.S. PATENT DOCUMENTS

| | | | | |
|---|---|---|---|---|
| 4,398,544 A * | 8/1983 | Nugent et al. | | 600/576 |
| 5,122,123 A | 6/1992 | Vaillancourt | | |
| 5,125,415 A * | 6/1992 | Bell | | 600/579 |
| 5,738,144 A * | 4/1998 | Rogers | | 137/614.03 |
| 6,869,426 B2 * | 3/2005 | Ganem | | 604/533 |
| 7,004,934 B2 * | 2/2006 | Vaillancourt | | 604/533 |
| 7,396,051 B2 * | 7/2008 | Baldwin et al. | | 285/354 |
| 7,500,961 B2 * | 3/2009 | Nemoto | | 604/151 |
| 7,588,563 B2 * | 9/2009 | Guala | | 604/535 |

(Continued)

FOREIGN PATENT DOCUMENTS
EP 0798013 10/1997
(Continued)

OTHER PUBLICATIONS
International Search Report dated Feb. 27, 2007.

*Primary Examiner* — Nicholas D Lucchesi
*Assistant Examiner* — Victoria P Campbell
(74) *Attorney, Agent, or Firm* — LIsa E. Winsor, Esq.

(57) ABSTRACT

Certain embodiments of the present invention include a male luer connector having a valve arrangement for keeping a passage that extends through the male luer connector closed when the male luer connector is not attached to a corresponding female luer connector. This passage of the male luer connector may opened by connecting the male luer connector to a female luer connector. The valve arrangement of the male luer connector may include a movable sealing element arranged around a central fluid conduit. In some embodiments, the male luer connector may include a filter that is permeable to gas, but substantially impermeable to liquid, thus allowing gas to be purged from the male luer connector while substantially preventing liquid from leaking from the connector at least when the male luer connector is not connected to a female luer connector.

33 Claims, 10 Drawing Sheets

U.S. PATENT DOCUMENTS

| | | | |
|---|---|---|---|
| 7,666,170 B2 * | 2/2010 | Guala | 604/249 |
| 7,753,892 B2 * | 7/2010 | Newton et al. | 604/236 |
| 2003/0032940 A1 * | 2/2003 | Doyle | 604/533 |
| 2003/0060804 A1 * | 3/2003 | Vaillancourt | 604/533 |
| 2003/0093061 A1 * | 5/2003 | Ganem | 604/533 |
| 2004/0124389 A1 | 7/2004 | Phillips | |
| 2004/0172006 A1 * | 9/2004 | Bonaldo | 604/523 |
| 2005/0087715 A1 | 4/2005 | Doyle | |
| 2005/0090805 A1 * | 4/2005 | Shaw et al. | 604/523 |
| 2005/0228362 A1 * | 10/2005 | Vaillancourt | 604/533 |
| 2007/0043334 A1 * | 2/2007 | Guala | 604/533 |
| 2007/0161970 A1 * | 7/2007 | Spohn et al. | 604/533 |
| 2008/0200902 A1 * | 8/2008 | Mabuchi | 604/537 |
| 2008/0249508 A1 * | 10/2008 | Lopez et al. | 604/533 |
| 2008/0300542 A1 * | 12/2008 | Kitani et al. | 604/131 |
| 2009/0292274 A1 * | 11/2009 | Guala | 604/533 |

FOREIGN PATENT DOCUMENTS

| | | |
|---|---|---|
| EP | 0798013 A1 | 10/1997 |
| WO | 2006074935 | 1/2006 |
| WO | 2006074935 | 7/2006 |

* cited by examiner

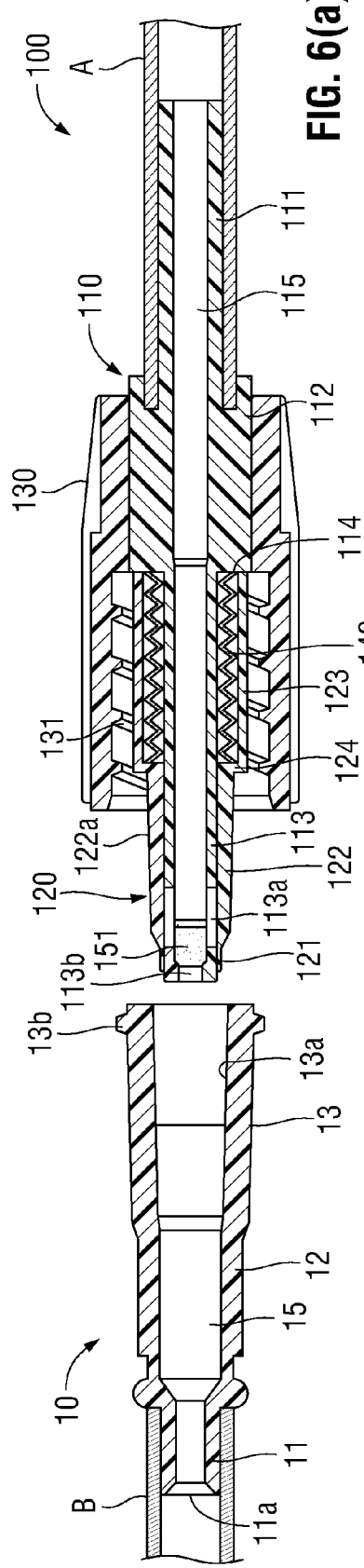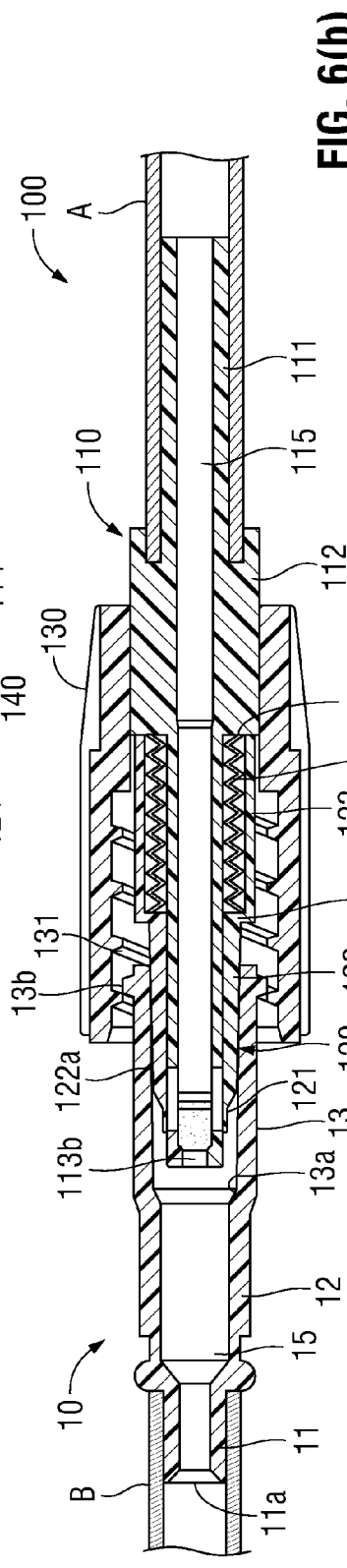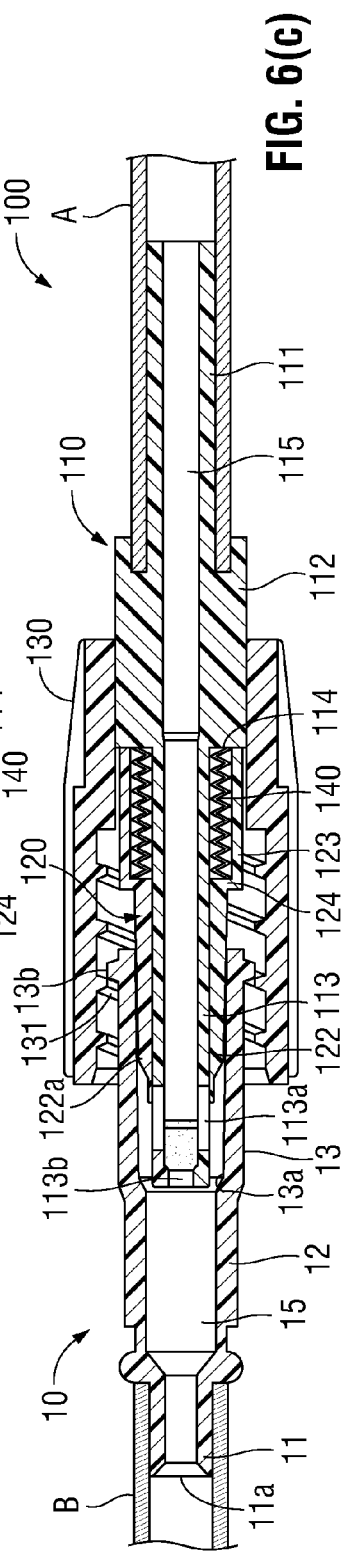

MALE LUER CONNECTOR

FIELD OF THE INVENTION

The present invention relates to tubing connectors and, more particularly, to a male luer connector for use with tubing for medical applications.

BACKGROUND

In the medical industry, connectors or fittings for communicatively coupling various types of medical tubing may be used to form pathways for infusion, blood transfusion, artificial dialysis or blood collection pathways. For example, representative connectors used in the medical industry often include luer connectors that have a tapered shape and substantially identical specifications.

Luer connectors may generally be divided into male luer connectors and female luer connectors. These different types of luer connectors may cooperate to communicatively couple separate pieces of medical tubing (medical treatment tubing) to form a single flow pathway. In other words, each luer may separately couple with the tubing and then couple with another luer to facilitate shared fluid flow through separate pieces of tubing. Specifically, one medical treatment tube may be attached to a male luer connector and another medical treatment tube may be attached to a female luer connector. Then, the one medical treatment tube and the other medical treatment tube may be connected by coupling the male luer connector and the female luer connector. In such a case, a tapered inner wall of a female luer part of the female luer connector and a tapered outside wall of a male luer member of the male luer connector may contact each other in a fluid-tight manner. Thus, fluid-tightness may be ensured by their contact when the medical treatment tubes are connected.

When the female luer connector is coupled with the male luer connector in a fluid-tight manner, a communicative connection between the connectors may be established. Accordingly, when liquid is sent to the male luer connector from the medical treatment tube connected to the male luer connector in this state, the liquid may flow into the female luer connector from the male luer connector and, in addition, flow from the female luer connector into the other medical treatment tube connected to the female luer connector. In this way, the medical treatment tube connected to the male luer connector and the other medical treatment tube connected to the female luer connector may be communicatively connected.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

A first aspect of the invention is directed to a male luer connector for coupling medical tubing. The male luer connector includes a main tube and a male luer member. The main tube includes a tube connection opening (e.g., an opening configured to couple with medical tubing), a vent opening (e.g., an opening arranged to facilitate gas flow out of the male luer connector), a main tube channel that extends along a first axis from the tube connection opening to the vent opening, a filter disposed within the vent opening, and a circumferential opening that extends through a wall of the main tube from the main tube channel to an outer side of the wall of the main tube along a second axis that is angled (i.e., non-parallel) with respect to the first axis. The filter preferably includes material that is gas permeable but prevents or resists liquid migration. In some embodiments, the filter may include a fibrous material or a combination of fibrous materials (e.g., nylon, polyester, Dacron™, non-woven cotton, Gortex™, paper). In some embodiments, the filter may include layers of material. For example, the filter may include a layer of Gortex™ arranged over charcoal (e.g., activated charcoal or a carbon-carbon composite) or a tube of Dacron™ surrounded by a sheath of non-woven cotton. In some embodiments, the filter may include an appropriately configured paper filter. The male luer member is disposed about the main tube such that an inner side of a wall of the male luer member is adjacent the outer side of the wall of the main tube. The male luer member includes a base opening, a tip opening, and a male luer member channel that extends along the first axis from the base opening to the tip opening. The base opening and the tube connection opening may be arranged on the same side of the male luer connector.

A second aspect of the invention is directed to a male luer connector for coupling medical tubing. The male luer connector of this second aspect includes a main tube and a male luer member. The main tube includes a tube connection opening, a vent opening, a main tube channel that extends along a first axis from the tube connection opening to the vent opening, and a circumferential opening that extends through a wall of the main tube from the channel to an outer side of the wall of the main tube along a second axis that is angled (i.e., non-parallel) with respect to the first axis. The male luer member is slidably disposed adjacent the main tube such that an inner side of the male luer member is adjacent the outer side of the wall of the main tube, and the male luer member is arranged to cover the circumferential opening when the male luer member is in an extended position. In other words, the male luer member is configured to move relative to (e.g., slide axially over) the main tube to open and close the circumferential opening. In some embodiments, the male luer member may be elastic and/or gas permeable. The elasticity of the male luer member may enable it to bias itself into a closed position over the circumferential hole. The gas permeable characteristic of the male luer member may facilitate purging of gas bubbles through the male luer member when it is covering the circumferential hole.

Yet a third aspect of the invention is directed to a male luer connector for coupling medical tubing. The male luer connector of this third aspect includes a main tube, a male luer member, and a filter. The main tube includes a tube connection opening, a tip end, a main tube channel that extends along a first axis from the tube connection opening to the tip end, and a circumferential opening that extends through a wall of the main tube from the channel to an outer side of the wall of the main tube along a second axis that is angled (i.e., non-parallel) with respect to the first axis. The male luer member is configured to move relative to the main tube between a closed position and an open position. For example, the male luer member may be configured to move axially relative to the main tube along the first axis between closed and open positions. In the closed position, the male luer member covers (i.e., occludes) the circumferential opening. In the open position, the male luer member reveals at least a portion of the circumferential opening. The gas permeable filter may be substantially impermeable to liquid to prevent liquid spillage during gas purging.

Still a fourth aspect of the invention is directed to a male luer connector having a valve arrangement for keeping a passage that extends through the male luer connector closed when the male luer connector is not attached to a corresponding female luer connector. This passage of the male luer connector is opened by connecting the male luer connector to a female luer connector. The valve arrangement of the male luer connector includes a movable sealing element arranged around a central fluid conduit. In some embodiments, the male luer connector includes a filter that is permeable to gas, but substantially impermeable to liquid. This filter allows gas to be purged from the male luer connector while substantially preventing liquid from leaking from the connector at least when the male luer connector is not connected to a female luer connector.

Still yet a fifth aspect of the invention is directed to a method of using a male luer connector. In this method, a main tube of the male luer connector is filled with medical fluid, and gas is purged from the main tube through a filter of the male luer connector. Further, a male luer member of the connector is contacted with a female luer member of a female luer connector while the male luer member is disposed over a hole in the main tube. The male luer is moved (e.g., slid) away from the hole, and the medical fluid is allowed to flow through the hole from the main tube to the female luer member. In some embodiments of this method, the medical fluid is prevented from going through the filter during gas purging by utilizing a filter that resists liquid transport and allows gas transport.

Yet a sixth aspect of the invention is directed to an injector system for medical applications. The injector system includes a syringe and a male luer connector of the invention that is in fluid communication with the syringe. The syringe may be a standard medical syringe, a syringe designed for power injectors, a prefilled syringe, or the like.

Various refinements may exist of the features noted above in relation to the various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

FIG. 6 is a cross section of the male luer connector in FIG. 3 and a female luer connector in various positions with respect to one another as they are being coupled.

DETAILED DESCRIPTION OF SPECIFIC EMBODIMENTS

Figure 1:
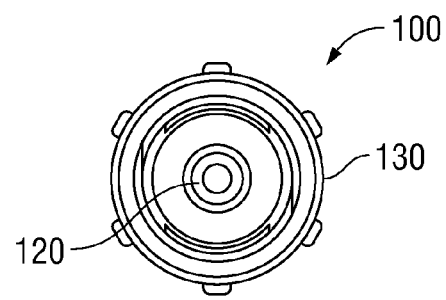
FIG. 1 is a front view of a male luer connector.

Traditional male luer connectors do not include a normally closed valve. This lack of a valve in traditional male luer connectors may be attributed to a need to prime tubing channels that are coupled to the male luer connectors. Indeed, advance treatment (priming) to fill the channel in a male luer connector with liquid to be supplied may be required before the male luer connector is connected to the female luer connector to eliminate air bubbles that have formed in the liquid and so forth. It has traditionally been thought that if a valve mechanism were attached to the tip of the male luer connector, this advanced treatment or priming could not be carried out.

From the situation described above, male luer connectors are typically open. Therefore, there may be a risk of bacteria growing in the opening at the tip of the female luer connector. Also, during the actual priming, the male luer connector may be filled until liquid spills from the tip opening of the male luer connector and filling is stopped at the stage it is spilled for complete filling with medicine. The spilled amount of medicine may be wasted. There may also be a risk of bacteria growing where the medicine was spilled from the male luer connector.

Embodiments of the present invention have been devised with a male luer connector that is configured to prevent medical fluid spills during priming and, thus, prevent wasted medical fluids and bacteria growth resulting from adhered liquid medicine. Thus, the features of a male luer connector that pertain to the present invention may include a male luer connector that is used to connect one tube to another tube, which may be connected to the aforementioned one tube, and that may be detachably connected to a female luer connector that is connected to the aforementioned other tube, there are provided a main tube that may be provided with a first opening and a second opening and inside of which may be formed a channel that connects with the aforementioned one tube through the aforementioned first opening, a male luer member that has a round, tubular shape and that is mounted on the outer circumference of the aforementioned main tube and that has a tapered outer wall that can contact, in a fluid-tight manner, a tapered inner wall formed in the aforementioned female luer connector, and a valve mechanism that closes the aforementioned second opening when the aforementioned outer wall of the aforementioned male luer member and the aforementioned inner wall of the aforementioned female luer connector are not in contact in a fluid-tight manner, and that opens the aforementioned second opening to connect the aforementioned channel and the aforementioned female luer connector when the aforementioned outer wall of the aforementioned male luer member and the aforementioned inner wall of the aforementioned female luer connector are in contact in a fluid-tight manner.

In accordance with present embodiments, the male luer connector may include a male luer member, a main tube, and a valve mechanism. A channel may also be formed inside the main tube, which may have a first opening connected to one end of the channel and a second opening connected to the other. A male luer member that has a tapered outer wall may be mounted on the outer circumference of the main tube. The tapered shape formed on the tapered outer wall of the male luer member may correspond to the tapered shape of the tapered inner wall formed in the female luer connector, and may have a portion that has approximately the same taper angle and diameter. Therefore, the tapered outer wall of the male luer member can contact the tapered inner wall of the female luer connector in a fluid-tight manner.

The valve mechanism may close the second opening when the tapered outer wall of the male luer member is not in contact with the tapered inner wall of the female luer member. Therefore, when the male luer connector is separated and not coupled to the female luer connector, the second opening may be closed by the valve mechanism, so the liquid in the channel does not spill out through the second opening. Thus, spilling liquid medicine or the like and its adherence to the outer surface of the male luer connector can be prevented, and growth of bacteria can be prevented in the adhered portion.

In addition, the valve mechanism may open the second opening part and connect the channel formed in the main tube and the female luer connector when the tapered outer wall of the male luer member is in contact in a fluid-tight manner with the tapered inner wall of the female luer connector. Because of this, the one tube connected to the male luer connector and the other tube connected to the female luer connector may be connected, and liquid circulation may be produced between the one tube and the other tube. In this way, when the male luer connector of the present invention is separated and not coupled with a female luer connector, adhesion of liquid medicine and bacteria growth can be controlled to the extent possible because of specifications such that liquid medicine or the like is not spilled outside, and when coupled with a female luer connector, a channel may be formed and, thus, the function as a connector may be ably fulfilled.

In this case, a gas removal opening that connects the aforementioned channel to the outside could be formed in the aforementioned main tube and a filter that is permeable to gases and not permeable to liquids could be mounted in the aforementioned gas removal opening.

By using an assembly such as this, a gas, such as air, present in the channel space within the main tube can be discharged to the outside through the gas removal opening by priming. In this case, a filter that is gas permeable and liquid impermeable may be mounted in the gas removal opening, so liquid in the main pipe will not leak out through the gas removal opening during priming. It should be noted that priming may be performed while the male luer connector is not coupled with a female luer connector, so the second opening may be closed by the valve mechanism. Therefore, liquid may be prevented from leaking through the second opening. Thus, the liquid may be prevented from spilling and priming can be executed without wasting liquid. In addition, since liquid may be prevented from spilling from the second opening and the gas removal opening, bacteria growth in the spilled liquid may be avoided.

An assembly in which a valve mechanism is formed in the male luer member can also be used in accordance with present embodiments. An assembly with only a main tube and a male luer member with a valve function may be sufficient as the component to constitute a male luer connector that accomplishes the function and effects of present embodiments.

Therefore, the male luer connector can be manufactured at low cost. In this case, the aforementioned second opening could be formed in the outer circumferential surface of the aforementioned main tube and the aforementioned male luer member could be movable on the outer circumference of the aforementioned main tube to close and open the aforementioned second opening. Because the male luer member may be mounted on the outer circumference of the main tube, the male luer member can be provided with a function as a valve without any particular changes in the structure of the male luer member, which may be more beneficial, by forming the second opening to be closed by the valve mechanism in the outer circumferential surface of the main tube and using an assembly that facilitates moving of the male luer member so as to be able to close and open the second opening.

In addition, in accordance with present embodiments, the aforementioned male luer member may be configured to move in a direction to open the aforementioned second opening by the aforementioned male luer connector moving with the aforementioned outer wall of the aforementioned male luer connector contacting the aforementioned inner wall of the aforementioned female luer connector. With such configuration, the aforementioned contact may be maintained just by moving the female luer connector in a direction closer to the male luer connector so as to maintain the contact state between the tapered outer wall of the male luer connector and the tapered inner wall of the female luer connector, and the male luer member also may move and the second opening may be opened. Because of this, an assembly to move the male luer member and open the second opening separately may not be required.

In this case, an energizing mechanism to energize the aforementioned male luer member could additionally be furnished so that the aforementioned male luer member will close the aforementioned second opening. With such a feature, when the male luer connector is not coupled to the female luer connector, a state in which the male luer member closes the second opening may be maintained by the energizing force of the aforementioned energizing mechanism. Because of this, spilling of liquid medicine or the like from the second opening during priming or the like can be reliably prevented.

It may be desirable for the aforementioned energizing mechanism to be a bellows member disposed to cover the outer circumference of the aforementioned main tube. By providing the energizing mechanism with a bellows-shaped member, even if the bellows-shaped member is subjected to force opposing the energizing force and deforms, it may be folded without taking up space, so it can be attached without concerns about space needed to attach the energizing mechanism. The folds may always be the same portion and they may fold in the same way, so that they are not easily broken. Because of this, the reliability of the energizing mechanism can be improved. The energizing mechanism can also be constituted without using a spring component.

The male luer connector in accordance with present embodiments may also have a locking member that may be rotatably attached on the outer circumference of the aforementioned male luer member and inside of which a threaded part may be formed, and the aforementioned female luer connector can be coupled to the male luer connector by screwing together the aforementioned locking member and the female luer connector. With luer connectors, normally a male luer connector and a female luer connector are detachably coupled, so there may be a risk of their being disconnected at any time. On this point, with the abovementioned assembly, the female luer connector may be screwed to the male luer connector with the locking member, so the female luer connector and the male luer connector can be coupled securely.

When the locking member is rotated, the female luer connector may be screwed to the male luer connector and may move toward the male luer connector. Here, coupling of the male luer connector and the female luer connector may be accomplished just by rotating the locking ring by the direction that the female luer connector may move for the tapered outer wall of the male luer member and the tapered inner wall of the female luer connector to contact and the direction that the male luer member may move to close the second opening being the same direction as the direction the female luer connector may be moved by rotation of the locking member. Also, with this connection (connection of the tapered outer wall and tapered inner wall) maintained, the male luer member can move and open the second opening. That is, connection of the male luer connector and the female luer connector and opening of the second opening can be accomplished just by rotating the locking member.

The aforementioned gas removal opening could also be formed in the end surface of the aforementioned main tube. By forming the gas removal opening in the end surface of the main tube, gas remaining in the entire area of the main tube can be collected at the end surface and removed to the outside from there. Because of this, nearly all the gas can be removed by priming.

The aforementioned gas removal opening could also be formed in the outer circumferential surface of the aforementioned main tube. If the gas removal opening is formed in the outer circumferential surface of the main tube, the filter mounted in the gas removal opening may also be attached to the outer circumferential surface of the main tube. Because of this, when gas (air) may be removed using the filter, the gas pressure acts equally in the circumferential direction on the filter, the pressure can be sufficiently distributed, and there may be no portions to which pressure is applied locally. Because of this, filter reliability can be improved.

The aforementioned second opening can also be used as the aforementioned gas removal opening. That is, the second opening and the gas removal opening can be the same opening. By so doing, it may not be necessary to form openings separately and the molding cost can be reduced. Here, a filter may be attached in the gas removal opening, but because the filter may not be permeable to liquid, when such an arrangement may be used, the liquid in the channel in the main tube may be blocked by the filter and prevented from flowing outside. For such a problem, a configuration could be used such that the filter may be removed from the second opening (gas removal opening) when liquid is discharged through the second opening (for example, when the tapered outer wall of the male luer member and the tapered inner wall of the female luer member are in contact and the channel in the main tube and the female luer connector are connected).

In this case, an arrangement in which the male luer member is used as both the filter and the valve mechanism may be ideal. By using such an arrangement, the male luer member may be attached in the gas removal opening as a filter and may also close and open the second opening as a valve mechanism. Because of this, when liquid is discharged through the second opening, the male luer member serving as a valve member may move and the second opening may be opened, so the liquid can flow out through the second opening.

The aforementioned male luer member could also be molded using an elastic material. By molding the male luer member with an elastic material, adhesion with the female luer connector may be improved and the male luer connector and the female luer connector may be harder to separate when coupled.

An assembly in which the filter may be formed integrally or an assembly in which the aforementioned luer member itself may be a filter may be desirable for the aforementioned male luer member. By also using the male luer member as a filter, it may not be necessary to provide a separate filter, so the male luer connector can be manufactured at lower cost. When a filter is formed integrally with the male luer member, the male luer member may also be molded using a porous material. If the male luer member is made with a porous material, for example, a plastic material or another porous resin that has internal indentations, the male luer member can be manufactured with a simple process and at low cost.

The aforementioned main tube could also have a connection opening part that has the aforementioned first opening and a conduit part that has the aforementioned second opening and around the outer circumference of which the conduit part may be mounted the aforementioned male luer member, the aforementioned connection opening part and the aforementioned conduit part could be formed separately, and in addition, the conduit part could be arranged to be able to move relative to the aforementioned male luer member to close and open the aforementioned second opening. Because the main tube may be formed with the connection opening part and the conduit part separated, it may be possible for the conduit part itself to move independently. In this case, by closing and opening the second opening by independent movement of the conduit part, the conduit part can be moved to close the second opening part even when the male luer connector is not coupled to the female luer connector. Note that, in this case, an O-ring or another sealing member could also be furnished at the part where the conduit part slides to prevent liquid from leaking from the channel in the main tube.

Figure 2:
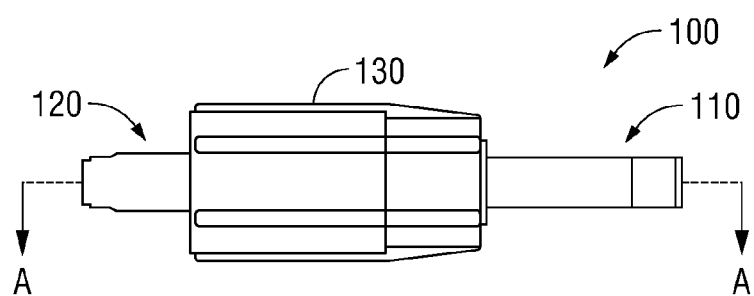
FIG. 2 is a plan view of a male luer connector.
Figure 3:
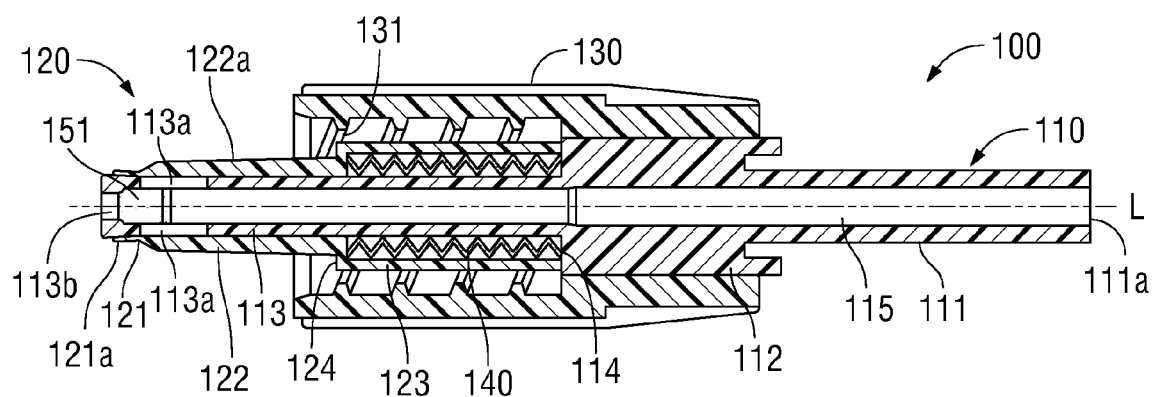
FIG. 3 is a cross section at A-A in FIG. 2.

Below, a male luer connector in accordance with present embodiments will be explained in detail in reference to the Figures. FIG. 1 is a front view of a male luer connector pertaining to one embodiment of the present invention, FIG. 2 is a plan view, and FIG. 3 is a cross section along A-A in FIG. 2. In the figures, male luer connector (100) includes a main tube (110), a male luer member (120) and a lock ring (130).

Main tube (110) may have a long, narrow-stepped, round, tubular shape, and a channel (115) may be formed on the inside. The channel (115) may be formed with a linear channel axis (L) as shown in FIG. 3. Main tube (110) may also include connection opening part (111), coupling part (112) and conduit part (113). Connection opening part (111) may form the portion on the right side of main tube (110) in FIG. 3 and may have a round, tubular shape with channel axis (L) as the axis. Connection opening part (111) may be the connection part by which a medical treatment tube or the like may be attached and through which liquid may be sent into channel (115) in main tube (110) from the medical treatment tube.

Conduit part (113) may be formed in the portion at the left side of main tube (110) in FIG. 3 and may have a hollow, round, tubular shape with channel axis (L) as the axis. A coupling part (112) may also be formed to the right side of conduit part (113) in FIG. 3. The outer diameter of coupling part (112) may be larger than the outer diameter of conduit part (113). Therefore, a stepped part (114) may be formed between conduit part (113) and coupling part (112). Coupling part (112) may also have a round, tubular shape with channel axis (L) as the axis to be coaxial with conduit part (113).

Channel (115) in main tube (110) may be formed through connection opening part (111), coupling part (112) and conduit part (113). A first opening (111a) that connects to one end of channel (115) may be formed on the connection opening part (111) side of main tube (110). An air removal opening (113b) that connects to the other end of channel (115) may be formed on the conduit part (113) side. Additionally, as shown, a second opening (113a) may be formed in conduit part (113) close to the aforementioned air removal opening (113b) and in the outer circumferential surface of conduit part (113). One or a plurality of second openings (113a) may be formed in the outer circumferential surface of conduit part (113).

Male luer member (120) may have a stepped, round, tubular shape and may be mounted on the outer circumference of conduit part (113) of main tube (110) so that channel axis (L) is its center axis. A tip part (121), a male side taper part (122) and a base part (123) may be formed on male luer member (120). Tip part (121) may define the part at the left end of male luer member (120) in FIG. 3. An opening (121a) may be formed at the left end in the figure of tip part (121). Male side taper part (122) may include the portion connected to the right side of tip part (121). Base part (123) may be formed on the right side of male side taper part (122). The outer diameter of base part (123) may be larger than the outer diameter of the right end of male side taper part (122). Therefore, a stepped part (124) that extends radially in the direction of the outer circumference relative to channel axis (L) may be formed between the male side taper part (122) and the base part (123).

In the illustrated embodiment, male side taper part (122) has a tapered outer wall (122a) that has a tapered shape with a point in which the outer diameter of the outer circumferential surface becomes smaller going from right to left in FIG. 3. It should be noted that the taper angle and diameter of tapered outer wall (122a) may be basically uniform according to standards. On the other hand, the inner diameter of male side taper part (122) may be approximately uniform in the direction of channel axis (L).

Figure 4:
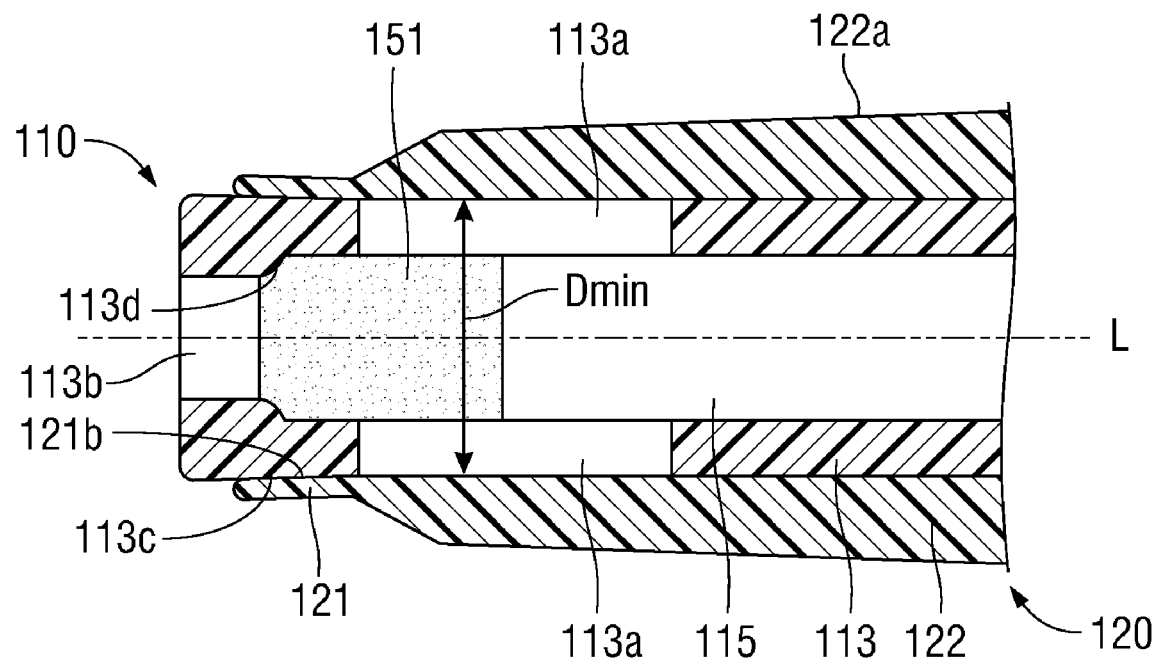
FIG. 4 is an enlarged view of a tip part of the male luer connector in FIG. 3.

FIG. 4 is an enlarged view of the tip part of male luer connector (100) (the portion toward the left in FIG. 3). Tip part (121) of male luer member (120) may have an inverse tapered inner wall (121b) in which the inner diameter becomes slightly larger going from right to left in the figure. Therefore, in the illustrated embodiment, the inner diameter of tip part (121) may be minimum inner diameter (Dmin) at the boundary with male side taper part (122). The inner diameter of male side taper part (122) may be approximately equal to aforementioned minimum inner diameter (Dmin) and may be uniform in the direction of axis (L).

At the same time, the outer circumference toward the left end of conduit part (113) of main tube (110) in FIG. 4 may have an inverse tapered outer wall (113c) formed such that the outer diameter becomes slightly larger going from the right to the left in the figure. The inverse taper shape of the inverse tapered outer wall (113C) may have a part corresponding to the inverse tapered shape of inverse tapered inner wall (121b). It should be noted that inverse tapered outer wall (113c) may be formed at the portion corresponding to tip part (121) of male luer member (120) (only the portion on the left side of inverse tapered outer wall (113) in FIG. 4). The outer diameter of the portion of conduit part (113) to the right of inverse tapered wall (113c) in the figure may have a diameter equal to the aforementioned minimum inner diameter Dmin and may be uniform in the direction of axis (L).

Therefore, when inverse tapered inner wall (121b) and inverse tapered outer wall (113c) are engaged, movement by both in a direction that would bring them closer together may be restricted. That is, operations wherein main tube (110) may move toward the right in FIG. 4 relative to male luer member (120) or male luer member (120) may move toward the left in FIG. 4 relative to main tube (110) may be controlled. However, operation in the direction in which both move away from each other, that is, operation wherein main tube (110) may move toward the left in FIG. 4 relative to male luer member (120) and operation whereby male luer member (120) may move toward the right in FIG. 4 relative to main tube (110), may be permitted.

When inverse tapered inner wall (121b) and inverse tapered outer wall (113c) are engaged, they may rub against each other. In the illustrated embodiment, the inner wall surface of male side taper part (122) may contact the outer wall surface of conduit part (113). Therefore, the second opening (113a) formed in conduit part (113) may be covered and hidden by inverse tapered inner wall (121b) and the inner wall surface of male side taper part (122) and, thus, may be closed. Accordingly, in the state shown in FIG. 4, liquid in channel (115) of main tube (110) may be prevented from spilling out through second opening (113a).

As shown in FIG. 3, base part (123) of male luer member (120) may be larger in diameter than male side taper part (122) due to stepped part (124). Because of this, a round, tubular space may be formed between base part (123) and conduit part (113) of main tube (110). A round, tubular bellows member (140) may be disposed inside this round, tubular space. This bellows member (140) may be formed of rubber. Bellows member (140) may also have a round, tubular shape that covers the outer circumference of conduit part (113). Its outer circumferential surface may have a bellows shape so that it can exhibit an elastic force in the direction of the tube axis. In addition, one end of bellows member (140) may contact stepped part (124) of male luer member (120) and its other end may contact stepped part (114) of main tube (110).

Bellows member (140) may be arranged in the male luer connector (100) such that the bellows member (140) exhibits a tensile force in the state shown in FIG. 3. Therefore, male luer member (120) can move toward the left in FIG. 3 relative to main tube (110) due to this expansion force. However, as described above, movement by male luer member (120) toward the left in FIG. 3 relative to main tube (110) may be restricted by the engagement of inverse tapered inner wall (121b) of male luer member (120) and of inverse tapered outer wall (113c) of main tube (110). Thus, while male luer member (120) may be configured such that it cannot move toward the left from the state shown in FIG. 3, an energizing force toward the left in FIG. 3 may always be provided by bellows member (140). Thus, a state in which second opening (113a) is closed by male luer member (120) may be maintained by this energizing force.

Lock ring (130) may be attached to cover the outer circumference of main tube (110) and male luer member (120) as shown in FIG. 3. In the illustrated embodiment, lock ring (130) has a round, tubular shape and may be attached to main tube (110) to be able to rotate around channel axis (L). A threaded part (131) may also be formed around the inner circumference of lock ring (130). Threads may be formed in threaded part (131) to facilitate screwing onto a projecting part of a female luer connector, as described below, to couple the female luer connector to male luer connector (100). A fastening piece, not shown, may also be formed on lock ring (130). Lock ring (130) may be fastened to coupling part (112) of main pipe (110) by this fastening piece. Because of this fastening, lock ring (130) may be enabled to move axially within a prescribed range relative to main tube (110). However, axial movement beyond the prescribed range may be restricted. Indeed, loosening of lock ring (130) from main tube (110) may be prevented in this way.

As can be seen from FIG. 4, a step (113d) may be formed on the inner wall toward the tip (toward the left in FIG. 4) of conduit part (113). A filter (151) may be disposed in channel (115) to engage with the step (113d). Filter (151) may be attached to the inner wall of conduit part (113) in a fluid-tight manner to close air removal opening (113b). Filter (151) may be formed with a porous resin material to have outstanding gas permeability but to be impermeable to liquid. Therefore, gas inside channel (115) can be discharged outside through filter (151). In contrast, liquid inside channel (115) may be prevented from passing through filter (151) and, thus, prevented from discharging outside through filter (151).

Figure 5:
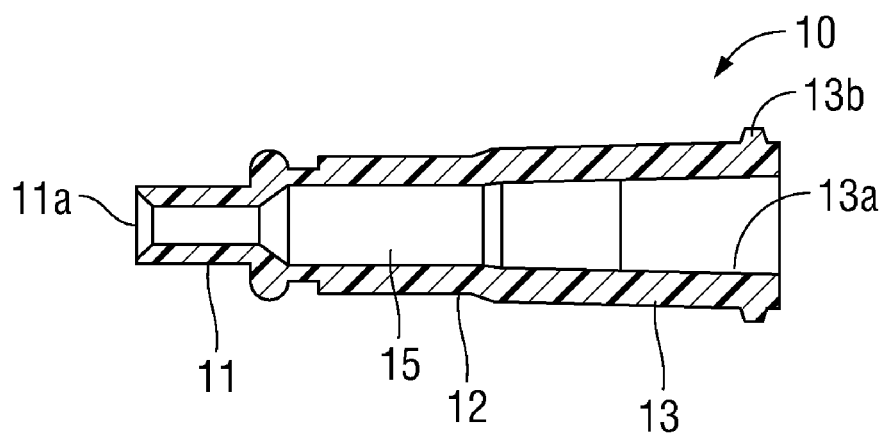
FIG. 5 is a cross section of a female luer connector.

FIG. 5 is a cross section of female luer connector (10) that may be coupled to male luer connector (100) in accordance with present embodiments. Female luer connector (10) may have a horn shape. As shown in the illustrated embodiment, the inner diameter of luer connector (10) may become larger from one side to another (left to right in FIG. 5). Luer connector (10) may have a connection opening part (11), a coupling part (12) and a female side taper part (13). Further, luer connector (10) may include a channel (15) formed inside. Connection opening part (11) may form the portion on the left side of female luer connector (10) in FIG. 5, and an opening (11a) in channel (15) may be formed at its left end. Connection opening part (11) may couple with a medical treatment tube or another tube and supply liquid from channel (15) to the medical treatment tube via the coupling.

Female side taper part (13) may form the portion on the right side of female luer connector (10) in FIG. 5. Female side taper part (13) may have a tapered inner wall (13a), the internal diameter of which becomes smaller going from right to left in FIG. 5. It should be noted that in this specification, the diameter decreasing from right to left in a figure may be referred to as a tapered shape, and the diameter increasing from right to left in a figure may be referred to as an inverse tapered shape. Tapered inner wall (13a) may include a portion with a taper angle and diameter corresponding to tapered outer wall (122a) formed on male side taper part (122) of male luer member (120). A projecting part (13b) that protrudes outward in the diametral direction may be formed on the outer circumference of female side taper part (13). In this embodiment, projecting part (13b) may be furnished at two positions that are symmetrical on the outer circumference of female side taper part (13). Further, projecting part (13b) at both positions may be configured to engage with threaded part (131) of lock ring (130) when female luer connector (10) may be coupled with male luer connector (100).

In the aforementioned assembly, priming may be performed as a measure to remove gas in channel (115) formed in male luer connector (100) before male luer connector (100) and female luer connector (10) are coupled and to fill channel (115) with the liquid to be circulated. This priming may be performed after a medical treatment tube is connected to connection opening part (111) of main tube (110) of male luer connector (100). This priming may be achieved by supplying the liquid to be circulated from the medical treatment tube and applying liquid pressure to channel (115).

When liquid is supplied from the medical treatment tube and liquid pressure is applied inside channel (115) by priming, the pressure inside channel (115) may become higher than the pressure outside due to the extra liquid pressure. However, as shown in FIGS. 3 and 4, second opening (113a) formed on the outside circumference of conduit part (113) may be covered by the inverse tapered inner wall (121b) of tip part (121) and the inner wall of male side taper part (122) of male luer member (120). Thus, second opening (113a) may be in a closed state, such that liquid or gas in channel (115) is prevented from discharging through second opening (113a).

Filter (151) may have outstanding gas permeability properties and may be attached in air removal opening (113b) formed in the end surface of conduit part (113). Therefore, gas inside channel (115) may pass through filter (151) and be discharged outside through air removal opening (113b). In this case, since filter (151) may be impermeable to liquid, liquid may be prevented from leaking out with gas that is discharged. Substantially all of the gas in channel (155) may be discharged out through filter (151) and priming may be completed when the liquid to be filled is approximately adjacent to filter (151).

Next, primed male luer connector (100) may be coupled to female luer connector (10) in accordance with present embodiments. Indeed, a procedure for coupling a medical treatment tube connected to male luer connector (100) with a medical treatment tube connected to female luer connector (10) may be performed, as illustrated in FIG. 6. Specifically, FIG. 6 shows relative positions of male luer connector (100) and female luer connector (10) during various steps of a process for coupling male luer connector (100) to female luer connector (10). FIG. 6(a) shows the two luer connectors before they are coupled. FIG. 6(b) shows the two luer connectors coupled. However, in FIG. 6(b) channel (115) of male luer connector (100) is not connected to channel (15) of female luer connector (10). FIG. 6(c) shows the two luer connectors coupled such that channel (115) and channel (15) are connected.

After male luer connector (100) and female luer connector (10) are brought to face as shown in FIG. 6(a), male luer connector (100) may be moved further toward the left in the figure, and tip part (121) and male side taper part (122) of male luer member (120) may be put inside female side taper part (13) of female luer connector (10). With this, as shown in FIG. 6(b), tapered outer wall (122a) of male side taper part (122) of male luer connector (100) may contact tapered inner wall (13a) of female side taper part (13) of female luer connector (10). As described above, the taper shape of tapered inner wall (13a) may correspond to the taper shape of tapered outer wall (122a), so when they are engaged, tapered outer wall (122a) and tapered inner wall (13a) contact over essentially the entire surface. Because of such full-surface touching, male side taper part (122) and female side taper part (13) contact.

In the illustrated embodiment of FIG. 6(b), projecting part (13b) formed on the outer circumference of female side taper part (13) of female luer connector (10) may be positioned substantially in the middle in the axial direction of male side taper part (122). At this position, projecting part (13b) can be caught by thread part (131) formed in the inner circumference of lock ring (130). Therefore, lock ring (130) may be moved along main tube (110) within an allowable range in the axial direction, the left end of threaded part (131) in the figure and projecting part (13b) may be brought to face each other, and lock ring (130) may be rotated. Then projecting part (13b) may be engaged with threaded part (131), and female luer connector (10) and male luer connector (100) may be more securely coupled.

Projecting part (13b) may be raised up in threaded part (131) by rotation of lock ring (130) and may move toward the right in FIG. 6 along the axis of rotation of threaded part (131). Along with this, all of female luer connector (10) may move closer (to the right in FIG. 6) to male luer connector (100). Here, female side taper part (13) of female luer connector (10) may be in contact with male side taper part (122) of male luer connector (100) and the two parts may be prevented from approaching each other beyond that. Because of this, while the contact state between male side taper part (122) and female side taper part (13) is maintained, male luer member (120) may move to the right in FIG. 6(*b*) as female luer connector (10) moves.

Male luer member (120) may be subjected to an energizing force toward the left in FIG. 6 by bellows member (140) and may move toward the right against the energizing force as lock ring (130) rotates. In this case, lock ring (130) and main tube (110) in which lock ring (130) may be engaged may not move. Therefore, male luer member (120) may move toward the right in the figure relative to main tube (110). Then, when this movement has advanced a prescribed amount, second opening (113*a*) that was closed by male luer member (120) may be opened and channel (115) in main tube (110) may be connected to channel (15) of female luer connector (10) through second opening (113*a*). This may be descriptive of the state in FIG. 6(*c*).

Thus, in the state in FIG. 6(*c*), if liquid is supplied from medical treatment tube (A) that is connected to male luer connector (100), liquid in channel (115) formed in main tube (110) of male luer connector (100) may flow into channel (15) in female luer connector (10) from second opening (113*a*). It then may flow into medical treatment tube (B) connected to female luer connector (10). In this way, medical treatment tube (A) at male luer connector (100) and medical treatment tube (B) at female luer connector (10) may be connected.

Since male luer connector (100) of this embodiment may be configured so that second opening (113*a*) of main tube (110) may be closed by the inner wall of male luer member (120), with male luer connector (100) separate and not coupled to female luer connector (10), male luer member (120) may function as a valve mechanism to close second opening (113*a*). Because of this, the liquid in channel (115) may be prevented from spilling out through second opening (113*a*). Thus, spilling of liquid medicine and bacteria growth where it adheres can be prevented.

Male luer member (120) may move and open second opening (113*a*) when tapered outer wall (122*a*) and tapered inner wall (13*a*) are in contact in a fluid-tight manner, and channel (115) at main tube (110) and channel (15) at female luer connector (10) may be connected. Because of this, medical treatment tube (A) may be connected to male luer connector (100) and medical treatment tube (B) may be connected to female luer connector (10) and fluid circulation may be produced between tubes (A) and (B). When male luer connector (100) is coupled with female luer connector (10) in this way, a channel may be opened and, thus, function as a connector may be ably achieved.

During priming, gas, such as air, present in channel (115) in main tube (110) may pass through filter (151) and may be discharged outside through air removal opening (113*b*). On the other hand, liquid in channel (115) may be prevented from passing through liquid-impermeable filter (151). Accordingly, liquid in main tube (110) may be prevented from leaking out through gas removal opening (113*b*) during priming. Further, because second opening (113*a*) may be closed by male luer member (120) in this case, liquid may also be prevented from leaking through second opening (113*a*). Thus, priming can be executed while preventing needless consumption of liquid such as by liquid spilling. In addition, growth of bacteria in the spilled liquid may be prevented.

Because the assembly provides male luer member (120) with a function as a valve mechanism to close or open second opening (113*a*), a valve mechanism to accomplish the aforementioned function need not be furnished separately. Therefore, the male luer connector can be manufactured at low cost.

In addition, second opening (113*a*) may be formed in the outer circumferential surface of conduit part (113) of main tube (100) and male luer member (120) may be movable on the outer circumference of conductor part (113) to the left in FIG. 6(*a*) to be able to close and open second opening (113*a*). With such an arrangement, male luer member (120) can function as a valve without especially changing the structure of male luer member (120).

Male luer member (120) also may move in a direction to open second opening (113*a*) by female luer connector (10) moving as lock ring (130) and may be rotated when tapered outer wall (122*a*) of male luer member (120) and tapered inner wall (13*a*) of female luer connector (10) are in contact. Because of this, second opening (113*a*) may be opened while the aforementioned contact may be maintained. Thus, no separate mechanism to move male luer member (120) in order to open second opening (113*a*) may be required in accordance with some embodiments.

Male luer connector (100) in the illustrated embodiment also may have a bellows member (140) serving as an energizing mechanism to energize male luer member (120) in a direction whereby male luer member (120) will move to open second opening (113*a*) (to the left in FIG. 3). Because of bellows member (140), when male luer member (100) is not coupled to female luer connector (10), second opening (113*a*) may be kept closed by male luer member (120). Because of this, spilling of liquid medicine or the like through second opening (113*a*) during priming or the like can reliably be prevented.

Aforementioned bellows member (140) may also be disposed to cover the outer circumference of main tube (110), one end may contact stepped part (114) of main tube (110), the other end may contact stepped part (124) of male luer member (120), and the outer circumference may be formed into a bellows shape. By using such a shape, it folds without taking up space even when the bellows-shaped portion on the outer circumference may be subjected to force against the energizing force and deforms. Thus, a bellows member (140) such as this can be attached without concern for the attachment space. The folds may consistently be the same size and they may fold in the same way, so they may not be easily broken. Because of this, the reliability of bellows member (140) can be improved.

With male luer connector (100) of this embodiment, female luer connector (10) can be coupled to male luer connector (100) by screwing lock ring (130) and female luer connector (10) together. Because of this, female luer connector (10) and male luer connector (100) can be coupled securely.

In the illustrated embodiment, the direction in which female luer connector (10) moves by rotation of lock ring (130) and the direction that female luer connector (10) moves in order for tapered inner wall (13*a*) of female side taper part (13) and tapered outer wall (122*a*) of male side taper part (122) to connect may be the same direction as the direction that male luer member (120) may move to open second opening (113*a*) (to the right in FIG. 6). Therefore, coupling of male luer connector (100) and female luer connector (10) can be completed just by rotating lock ring (130), and male luer member (120) can be moved to open second opening (113*a*) while maintaining the coupling of tapered outer wall (122*a*) and tapered inner wall (13*a*).

Air removal opening (113*b*) may also be formed at the end surface of conduit part (113) of main tube (110). Because of this, gas remaining in the main tube (110) can be collected at the end surface from where it can be removed, and nearly all gas can be removed by priming.

Male luer member (120) may also be energized toward the front of main tube (110) (toward the left in FIG. 3) by an energizing force from bellows member (140), and loosening of male luer member (120) at the front of main tube (110) can be prevented by engagement of inverse tapered outer wall (113c) formed on the outer circumference at the tip part of conduit part (113) of main tube (110) and inverse tapered inner wall (121b) formed on the inside circumference at the tip part (121) of male luer member (120). Because of this, male luer member (120) can be set at the position at which inverse tapered outer wall (113c) and inverse tapered inner wall (121b) are engaged and in that position second opening (113a) can be securely closed.

Figure 7:
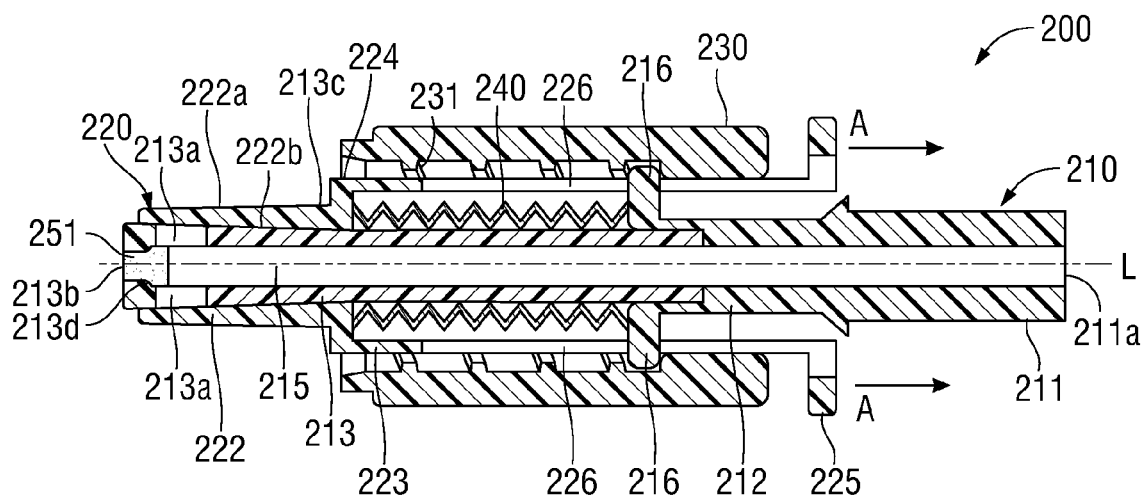
FIG. 7 is a cross section of a male luer connector.

FIG. 7 is a cross section of a male luer connector in accordance with present embodiments. As illustrated in FIG. 7, male luer connector (200) may include a main tube (210), a male luer member (220), and a lock ring (230). Main tube (210) may include connection opening part (211), coupling part (212) and conduit part (213). The placement and constitution of connection opening part (211), coupling part (212) and conduit part (213) may be basically the same as the placement of the related features discussed above with respect to FIGS. 1-6. Inside main tube (210), channel (215) may be formed such that it has a channel axis (L) and it passes through connection opening part (211), coupling part (212) and conduit part (213).

Male luer member (220) may have a stepped, round, tubular shape and may be mounted on the outer circumference of conduit part (213) of main tube (210) to cover it. A male side taper part (222), a base part (223) and a lever part (225) may also be formed on male luer part (220). Male side taper part (222) may be a round, tubular portion formed to the left side of male luer member (220) in FIG. 7 and it may have a tapered outer wall (222a), the outer diameter of which decreases going from right to left in FIG. 7, on its outer circumference, the same as male side taper part (122) in the aforementioned embodiments discussed with respect to FIGS. 1-6. In addition, male side taper part (222) may have an inverse tapered inner wall (222b), the inner diameter of which increases going from right to left in FIG. 7, on its outer circumference.

Base part (223) may be formed at the right side of male side taper part (222) in FIG. 7. Base part (223) may be formed in a round, tubular shape coaxially with male side taper part (222) and its outer diameter may be larger than the outer diameter of male side taper part (222). Therefore, a stepped part (224) that extends radially toward the outside in the diametral direction relative to channel axis (L) may be formed between male side taper part (222) and base part (223). In addition, to the right side of base part (223) in FIG. 7 may be formed a lever part (225). Lever part (225) may be formed extending outward diametrally relative to channel axis (L) from the right end of base part (223). A long, narrow slit (226) may also be formed in the axial direction from base part (223) to lever part (225).

As shown in FIG. 7, approximately the left half of conduit part (213) of main tube (210) in the figure, in actual terms, the outer circumference in the part facing inverse tapered inner wall (222b) of male side taper part (222), may have an inverse tapered outer wall (213c) formed in an inverse tapered shape, the outer diameter of which increased going from right to left in the figure. The taper shape of inverse tapered outer wall (213c) may correspond to the taper shape of inverse tapered inner wall (222b) of male side taper part (222). The minimum outer diameter of inverse tapered outer wall (213c) and the minimum inner diameter of inverse tapered inner wall (222b) may be approximately matching diameters.

FIG. 7 shows a state in which inverse tapered outer wall (213c) of conduit part (213) and inverse tapered inner wall (222b) of male side taper part (222) are in contact. When the taper parts that correspond are in contact in this way, movement by the taper surfaces to come closer may be restricted. In other words, operation wherein main tube (210) moves toward the right in FIG. 7 relative to male luer member (220) and operation wherein male luer member (220) moves to the left in FIG. 7 relative to main tube (210) may be restricted. However, the directions in which the taper surfaces separate, that is, operation wherein main tube (210) moves toward the left in the figure relative to male luer member (220) and operation wherein male luer member (220) moves to the right in the figure relative to main tube (210), may be permitted.

A second opening (213a) formed on the outer circumference of conduit part (213) may be covered by inverse tapered inner wall (222b), which is the inner circumferential wall of male side taper part (222), and may be closed. Therefore, liquid in channel (215) of main tube (210) may be prevented from spilling out through second opening (213a). A round, tubular space may also be formed between the inner wall of base part (223) of male luer member (220) and the outer wall of conduit part (213) of main tube (210), and inside this round, tubular space a round, tubular shaped bellows member (240) may be housed. Male luer member (220) may be held in the position shown in FIG. 7 while subjected to an energizing force by the energizing force of bellows member (240) acting on male luer member (220). Because of this, a state in which male luer member (220) closes second opening (213a) may be maintained.

A projecting part (216) that protrudes outward diametrally relative to channel axis (L) may also be formed at the left side of coupling part (212) of main tube (210) in FIG. 7, that is, at the part connecting with conduit part (213). Four projecting parts (216) may be furnished at 90 degree intervals around the circumference. The projecting parts (216) may be configured for insertion into a slit (226) formed in base part (223) and lever part (225) of male luer member (220). The tip of projecting part (216) may protrude from slit (226).

Lock ring (230) may be attached to cover the outer circumference of male luer member (220) and main tube (210) as shown in FIG. 7. Lock ring (230) may have a round, tubular shape viewed overall, and a threaded part (231) may be formed on the inner circumference. As can also be seen from the figure, within threaded part (231) in the thread groove at the farthest right, the tip portion of projecting part (216) protruding from slit (226) of male luer member (220) may be engaged. Lock ring (230) may be fixed to be able to rotate and to be unable to move axially relative to main tube (210) by this engaging so that it will not come loose from main tube (210).

A step (213d) may be formed on the inner wall at the tip (left end in FIG. 7) of conduit part (213). A filter (251) may be disposed in channel (215) to engage in the step (213d) Filter (251) may be attached in a fluid-tight manner to the inner wall of conduit part (213) to close air removal opening (213b). Filter (251), like filter (151) discussed above, may have outstanding gas permeability properties and may be substantially impermeable to liquids.

In the embodiment illustrated by FIG. 7, priming may be performed before male luer connector (200) and female luer connector (10) are coupled. In this priming, as explained above, gas, such as air, in channel (215) may be transmitted through filter (251) and may be discharged outside from air removal opening (213b). In addition, because filter (251) may prevent liquid passage and second opening (213a) may be closed at the inner wall of male side taper part (222), the liquid in channel (215) may be prevented from flowing out through either air removal opening (213b) or second opening (213a), and spilling the liquid during priming may be avoided.

Figure 8:
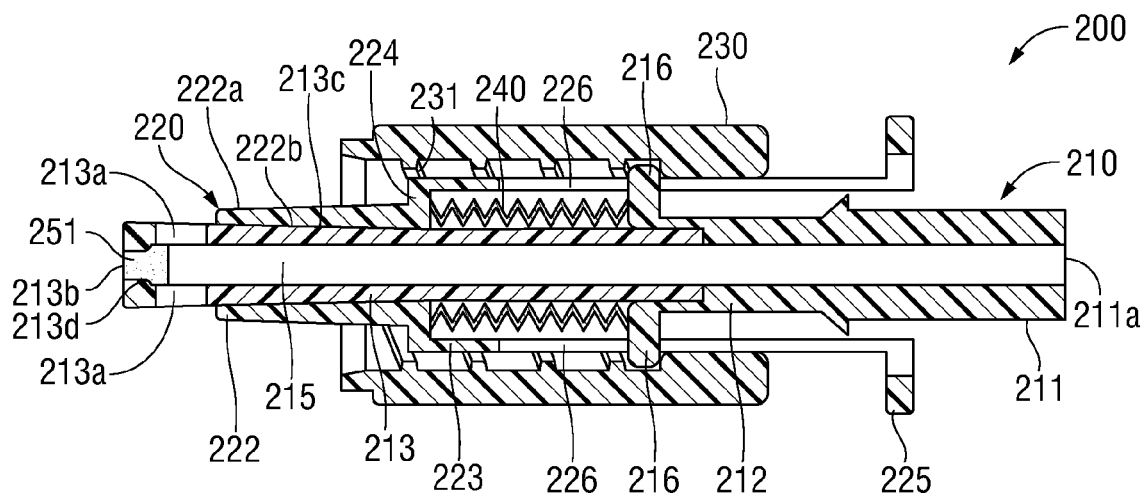
FIG. 8 is a cross section of a male luer connector with a lever part in an actuated position.

When priming is completed, bubbles may remain in channel (215). In this case, when channel (215) is already filled with liquid by priming, the bubbles remaining in channel (215) may resist movement toward filter (251) and discharge through filter (251) despite liquid pressure being applied. Thus, such residual bubbles may completely resist removal by priming. Accordingly, lever part (225) of male luer member (220) may be manually pulled to the right as indicated by arrow (A) in FIG. 7. With this operation, male luer member (220) may move to the right in the figure relative to main tube (210) to give the state shown in FIG. 8.

Then, second opening (213a) that was covered by the inner wall of male side taper part (222) of male luer member (220) may be opened by the movement of male luer member (220). Because of this, liquid in channel (215) of main tube (210) may flow out of second opening (213a) by the supply of liquid pressure from the medical treatment tube connected to connection opening part (211). Flow may be produced in channel (215) of main tube (210) by this outflow. Therefore, bubbles remaining in channel (215) may be moved by the flow in channel (215) and discharged outside through second opening (213a). The remaining bubbles may be discharged outside by operating lever part (225) manually in this way.

Such a residual bubble discharge measure should not be used frequently, from the aspect of excess liquid consumption and the growth of bacteria in the spilled portion, since the liquid in channel (215) may be spilled along with the residual bubbles, but in the event that priming may be performed and residual bubbles still remain, it may be useful in that the bubbles can be completely removed. Convenience may be improved by using a male luer connector with such a function.

Next, male luer connector (200), which has been completely primed, may be coupled to female luer connector (10). This may result in coupling a medical treatment tube connected to male luer connector (200) with a medical treatment tube connected to female luer connector (10). This operation may be the same as that explained with respect to aforementioned embodiments. FIG. 9 shows the operation of coupling male luer connector (200) to female luer connector (10). Specifically, FIG. 9(a) shows the two uncoupled, FIG. 9(b) shows the two coupled but with channel (215) of male luer connector (200) and channel (15) of female luer connector (10) not connected, and FIG. 9(c) shows coupling of the two completed and channel (215) and channel (15) connected.

Figure 9A:
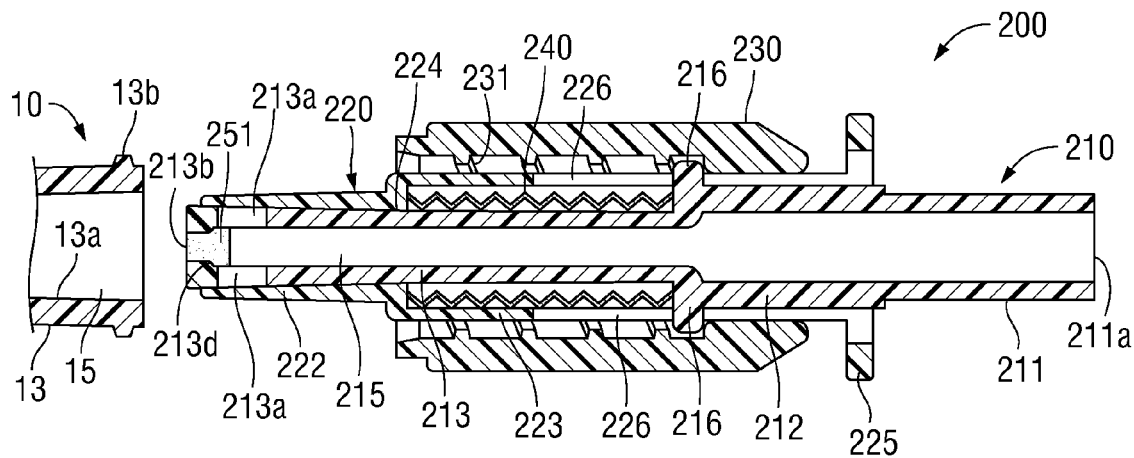
FIG. 9 is a cross section of the male luer connector in FIG. 7 and a female luer connector in various positions with respect to one another as they are being coupled.
Figure 9B:
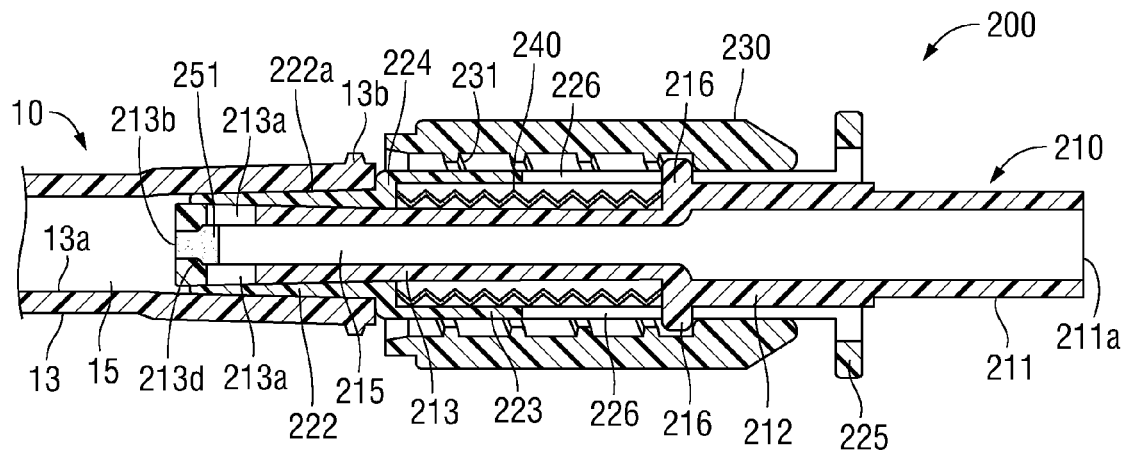

From the state shown in FIG. 9(a), male luer connector (200) may be moved further to the left in the figure and male side taper part (222) of male luer member (200) may enter female side taper part (13) of female luer connector (10). Then, as shown in FIG. 9(b), tapered outer wall (222a) of male side taper part (222) of male luer connector (200) may contact tapered inner wall (13a) of female side taper part (13) of female luer connector (10). Then, from the state in FIG. 9(b), projecting part (13b) of female luer connector (10) may be caught by threaded part (231) formed on the inner circumference of lock ring (230) and lock ring (230) may be rotated. Then, projecting part (13b) may be screwed into threaded part (231) by the rotation of lock ring (230) and female luer connector (10) and male luer connector (200) may be more securely coupled.

Projecting part (13b) may roll on threaded part (231) by the rotation of lock ring (230) and may move to the right in the figure, which is the direction of the axis of rotation of threaded part (231), and male luer member (220) may move to the right in the figure relative to main tube (210) along with this. Second opening (213a) of main tube (210) that is closed by male luer member (220) may be opened by the movement of male luer member (220) and channel (215) in main tube (210) may connect to channel (15) of female luer connector (10) through second opening (213a). This may describe the state illustrated in FIG. 9(c).

Figure 9C:
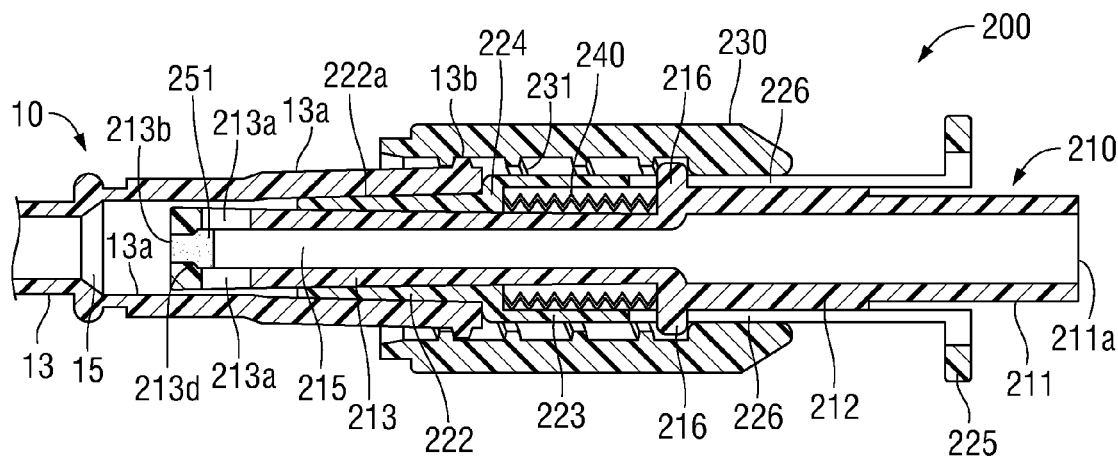

Thus, if liquid pressure is provided from the medical treatment tube (not shown) connected to male luer connector (200) in FIG. 9(c), the liquid in main tube (210) of male luer connector (200) may flow into channel (15) in female luer connector (10) through second opening (213a). It then may flow into the medical treatment tube (not shown) connected to female luer connector (10). The medical treatment tube at male luer connector (200) and the medical treatment tube at female luer connector (10) may be connected in this way.

In this embodiment, a lever part (225) may be furnished for male luer member (220) and by operating lever part (225) manually (or automatically), second opening (213a) can be opened even while male luer connector (200) is connected to female luer connector (10). Because of this, if there are residual bubbles that were not removed by priming, second opening (213a) may be opened by operation of lever (225) to produce a liquid flow in channel (215) and residual bubbles can be discharged through second opening (213a) with the liquid flow.

Also, because lever part (225) may be formed just to the right in the figure from base part (223), there may be the risk of base part (223) interfering with projecting part (216), but regarding this point, with this embodiment, a slit (226) may be furnished from base part (223) of male luer member (220) to lever part (225) in the direction of flow axis (L). Projecting part (216) may be disposed to go into slit (226). Therefore, even when lever part (225) is manipulated in the direction of flow axis (L), base part (223) of male luer member (220) and projecting part (216) do not interfere.

Figure 10:
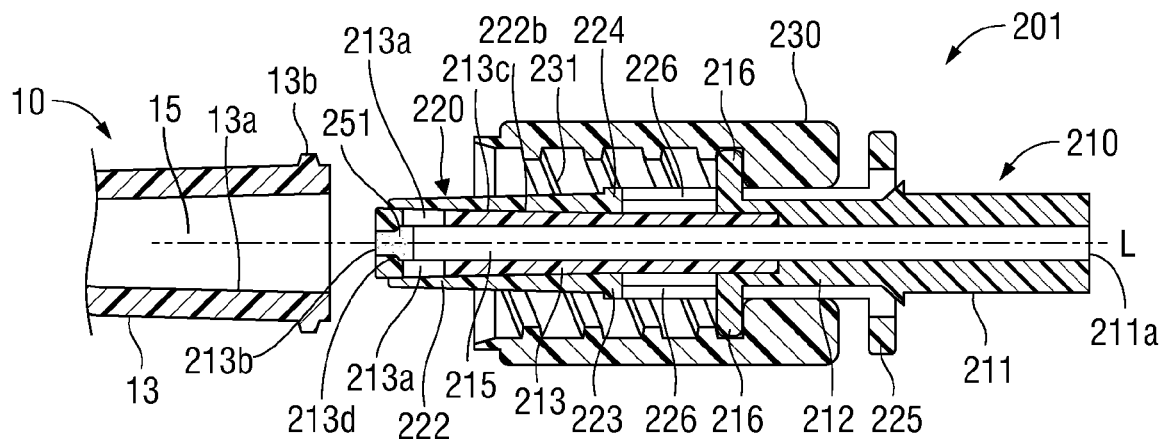
FIG. 10 is a cross section of a male luer connector.

FIG. 10 is a cross section of male luer connector (201) in accordance with present embodiments. The male luer connector (201) differs from the aforementioned embodiments in that bellows member (240) is not included. However, other than the lack of bellows member (240), the embodiment illustrated by FIG. 10 is essentially the same as that of previously discussed embodiments. Without bellows member (240), no energizing force may be generated for male luer member (220) toward the left in FIG. 10. Therefore, male luer member (220) may be more readily able to move axially relative to main tube (210).

However, some securing force may be exhibited by contact between inverse tapered inner wall (222b) formed on male side taper part (222) of male luer member (220) and inverse tapered outer wall (213c) formed in the region to the left of main tube (210) in FIG. 10. Thus, even when priming may be performed in this state, male luer member (220) may not move and second opening (213a) may not be opened. Then male luer member (220) may be coupled with female luer connector (10), and by rotating lock ring (230), male luer member (220) may move and second opening (213a) may be opened. The liquid in channel (215) may flow toward female luer connector (10) through second opening (213a) that may be opened in this way.

When male luer connector (201) is removed from female luer connector (10) after use, first, lock ring (230) may be rotated to unscrew threaded part (231) and projecting part (13b), and then main tube (210) may be pulled out while holding lever part (225). By doing this, second opening (213a) may be closed by male luer member (220) via the operation of pulling out main tube (210). Then, female luer connector (10) may be uncoupled while second opening (213a) remains closed. Because of this, liquid leakage can be prevented when male luer connector (201) is removed from female luer connector (10).

Therefore, if male luer member (220) has a structure that permits priming without requiring a bellows member or the like to energize main tube (210), the male luer connector can be configured to omit a bellows member. In particular, this type of component may be discarded after use, so in a design that does not require a bellows member such as this example, the male luer connector can be manufactured at a low cost.

Figure 11:
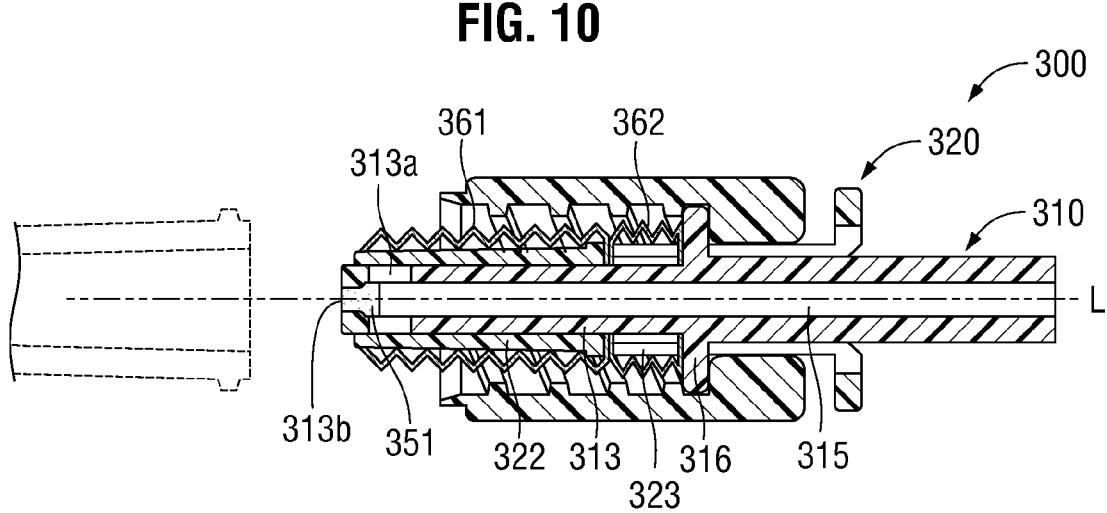
FIG. 11 is a cross section of a male luer connector.

FIG. 11 is a cross section of male luer connector (300) in accordance with present embodiments. In the illustrated embodiment of FIG. 11, male luer connector (300) includes a first bellows member (361) attached on the outer circumferential part of male side taper part (322) of male luer member (320). In addition, a second bellows member (362) may be attached to the outer circumferential part to the left in FIG. 11 of base part (323) of male luer member (320). First and second bellows members (361) and (362) may include a rubbery material and may have a round, tubular shape to enclose the outer circumference on the left side of base part (323), and male side taper part (322).

One end (the right end in FIG. 11) of first bellows member (361) may be attached between base part (323) and male side taper part (322) of male luer member (320). First bellows member (361) may be affixed to male luer member (320) in this part. One end (the left end in FIG. 11) of second bellows member (362) may touch the end of first bellows member (361), while its other end (the right end in FIG. 11) may contact projecting part (316) formed on main tube (310). Here, second bellows member (362) is by nature long in the state shown in FIG. 11, or a state that generates tensile force. Because of this, second bellows member (362) energizes first bellows member (361) and male luer member (320) to which first bellows member (361) may be affixed to the left in the figure.

Also, in the state shown in FIG. 11, male luer member (320) may close second opening (313a) formed in the outer circumference toward the left end of conduit part (313) in the figure of main tube (310). This state may be maintained by the energizing force of aforementioned first and second bellows members (361), (362) so that second opening (313a) may be securely closed by male luer member (320). The embodiment illustrated in FIG. 11 may otherwise be basically the same as the embodiment illustrated in FIG. 7.

In the embodiment illustrated by FIG. 11, during priming, gas in channel (315), such as air, may pass through filter (351) and may be discharged outside through air removal opening (313b). Filter (351) may have outstanding gas permeability. In this case, filter (351) may resist transmission of liquid. Thus, liquid may be prevented from leaking outside along with the gas discharge.

Figure 12:
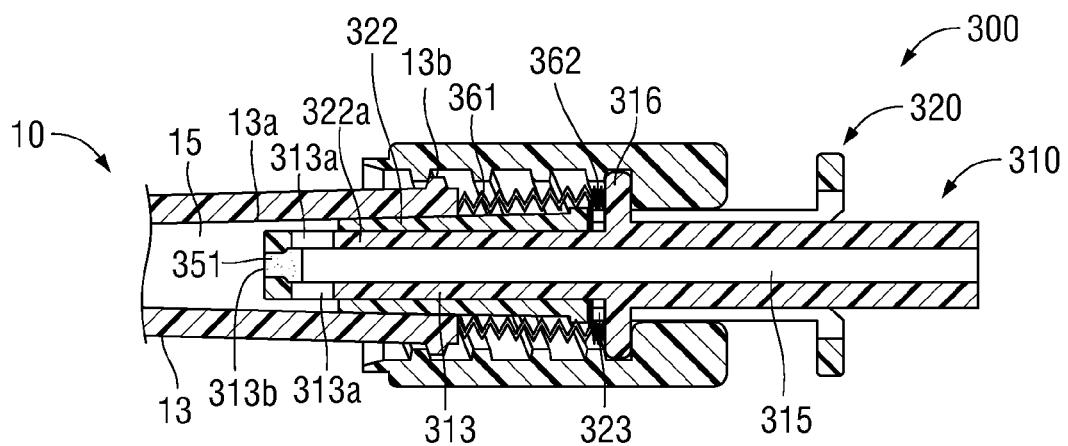
FIG. 12 is a cross section of a male luer connector and a female luer connector coupled together.

FIG. 12 is a cross section of male luer connector (300) coupled to female luer connector (10). As shown in the figure, when female luer connector (10) is moved so that female side taper part (13) of female luer connector (10) couples to male side taper part (322) of male luer connector (300), first bellows member (361) disposed on the outer circumference of male side taper part (322) may be pushed aside by the tip of female side taper part (13). Then, tapered inner wall (13a) of female side taper part (13) and tapered outer wall (322a) of male side taper part (322) may make contact. When movement continues, male luer member (320) may move to the right in the figure relative to main tube (310) and second opening (313a) may be opened. Then the liquid in channel (315) may flow out through second opening (313a) and toward channel (15) in female luer connector (10). In this way, present embodiments can also be implemented with an assembly that includes first and second bellows members (361), (362) as energizing members on the outer circumference of male luer member (320).

Figure 13:
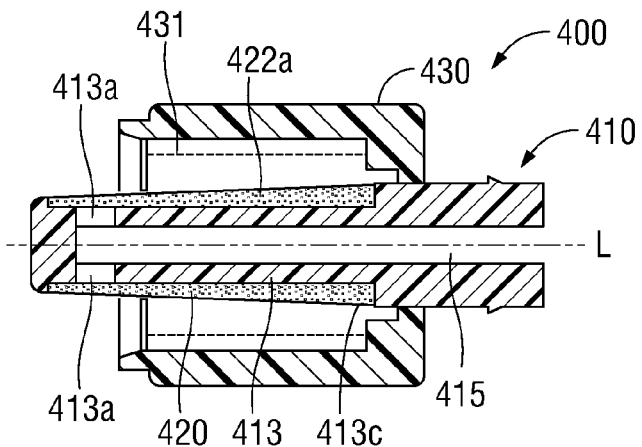
FIG. 13 is a cross section of a major part (tip part) of a male luer connector.

In accordance with some embodiments of the present invention, a luer may include an opening part that is utilized both for liquid flow out and gas (air) removal. Further, the male luer member may include an elastic material that has outstanding permeability. For example, FIG. 13 is a cross section of the major parts of male luer connector (400) that exemplifies such features. In the illustrated embodiment, the left end surface in FIG. 13, which is the tip of main tube (410), may be closed in male luer connector (400). A ring-shaped groove (413c) may also be formed around the circumference on the outer circumference of conduit part (413). Second opening (413a) may be formed in the bottom surface at the left end in the figure of ring-shaped groove (413c).

Male luer member (420) may have a round, tubular shape and may be placed and fit into ring-shaped groove (413c) formed in conduit part (413). The outer circumference of male luer member (420) may serve as tapered outer wall (422a), the diameter of which decreases going from right to left in FIG. 13. Male luer member (420) may be formed with a porous resin material that is elastically deformable and in which many indentations may be formed on the inside and on the surface. The porous resin material may have outstanding gas permeability because of these many indentations. However, it may be impermeable to liquid.

As described above, second opening (413a) may be formed as an opening in the bottom surface of ring-shaped groove (413c) formed on the outer circumference of conduit part (413). Male luer member (420) may be fit into ring-shaped groove (413c). In the state shown in the figure, the entire bottom surface of ring-shaped groove (413c) may be such that it is covered by the inner wall of male luer member (420). Therefore, second opening (413a) may be closed by male luer member (420).

In such an arrangement, during priming, gas in channel (415), such as air, may pass through second opening (413a) and meet the inner wall surface of male luer member (420). Here, male luer member (420) may have outstanding gas permeability, so the gas may pass through male luer member (420) and may be discharged outside. However, male luer member (420) may resist transmission of liquid. Accordingly, liquid may be prevented from leaking out with the discharge of gas.

Figure 14A:
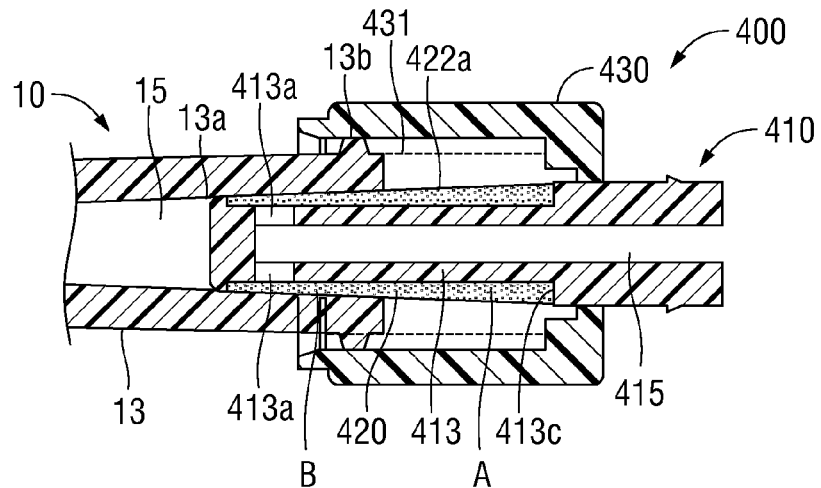
FIG. 14 is a cross section of the male luer connector in FIG. 13 and a female luer connector in various positions with respect to one another as they are being coupled.
Figure 14B:
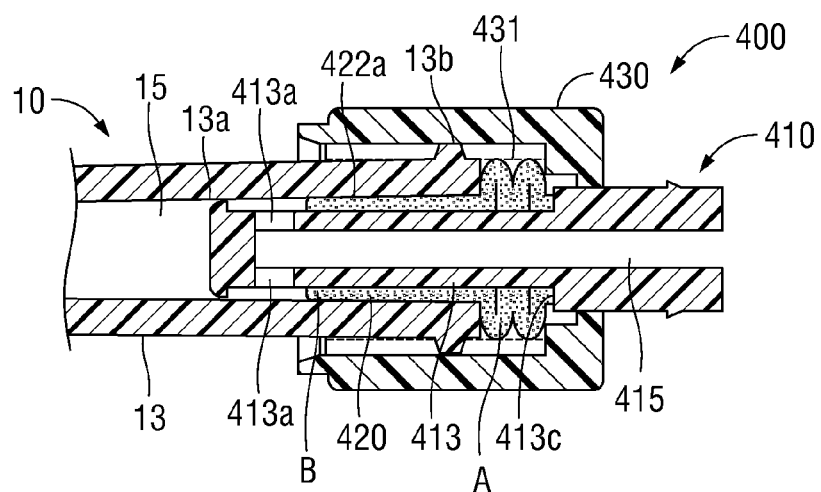

FIG. 14 illustrates component positioning during coupling of male luer member (400) to female luer connector (10). FIG. 14(a) shows the two connectors coupled without channel (415) of the male luer connector and channel (15) of the female luer connector being connected. FIG. 14(b) shows the two connectors coupled such that channel (415) and channel (15) are connected. When female luer connector (10) and male luer connector (400) are brought together, tapered inner wall (13a) of female side taper part (13) and tapered outer wall (422a) of male luer member (420) may ultimately make contact as shown in FIG. 14(a).

When lock ring (430) is rotated from the state shown in FIG. 14 (a), threaded part (431) formed in the inner wall of lock ring (430) may carry the projecting part (13b) formed on the outer circumference of female side taper part (13) so that female luer part (10) moves further to the right in FIG. 14. Along with this movement, male luer member (420) also may move to the right in FIG. 14 while the aforementioned contact is maintained.

However, male luer member (420) may be fit into ring-shaped groove (413c) formed in the outer circumference of conduit part (413), so even when male luer member (420) tries to move to the right in FIG. 14, it may be hindered by the side wall of ring-shaped groove (413c). Here, male luer member (420) in this embodiment may be formed with a porous resin material that may be elastically deformable. Therefore, portion (A) of male luer member (420) that is not contacting tapered inner wall (13a) of female side taper part (13) may buckle by movement to the right of female luer member (10) in FIG. 14. Then, as shown in FIG. 14(b), portion (A) may be folded and its length in the axial direction may be shortened.

Female luer member (10) may be moved to the right in FIG. 14 by the amount that portion (A) is folded, and the axial length may be shortened. In this case, contact between female side taper part (13) and male luer member (420) may be maintained and only portion (B) of male luer member (420) contacting female side taper part (13) may move toward the right in the figure relative to main tube (410) with female luer connector (10). Second opening (413a), which was previously closed by male luer member (420), may be opened by this movement. Therefore, the liquid in channel (415) of main tube (410) may flow out through second opening (413a). The liquid flowing out of second opening (413a) may flow into channel (15) of female luer connector (10).

With male luer connector (400) of this embodiment, during priming, air in channel (415) may pass through second opening (413a) formed in the outer circumferential surface of main tube (410) (conduit part (413)). Additionally the air may pass through male luer member (420) and get discharged outside. That is, the air removal opening (gas removal opening) may be formed in the outer circumferential surface of main tube (410) (conduit part (413)) in this embodiment. Because of this, gas pressure may act equally in the diametral direction on male luer member (420) that functions as a filter during priming, the pressure may be sufficiently distributed, and pressure may not be applied to any portions locally. Because of this, the reliability of the filter can be improved.

Because the assembly may be such that second opening (413a), which may be used as the liquid outlet, may also be used as the gas removal opening for air removal. It may not be necessary to form separate openings and, thus, the molding cost can be reduced. In addition, with this embodiment, male luer member (420) may be used as a filter. In other words, in addition to the function as a valve mechanism for opening and closing second opening (413a), male luer member (420) may also be provided with a function as a filter. For example, a filter may be formed integrally in male luer member (420). Thus, it may not be necessary to furnish a filter separately, and the male luer connector can be manufactured at low cost. Also, since male luer member (420) may be molded with a porous material, male luer member (420), which doubles as a filter, can be manufactured with a simple process at low cost.

In addition, since male luer member (420) may be molded with a resin material that is elastically deformable (elastic material), the adhesion when in contact with female side taper part (13) of female luer connector (10) may improve, and male luer connector (400) and female luer connector (10) can be better integrated when coupled.

Figure 15:
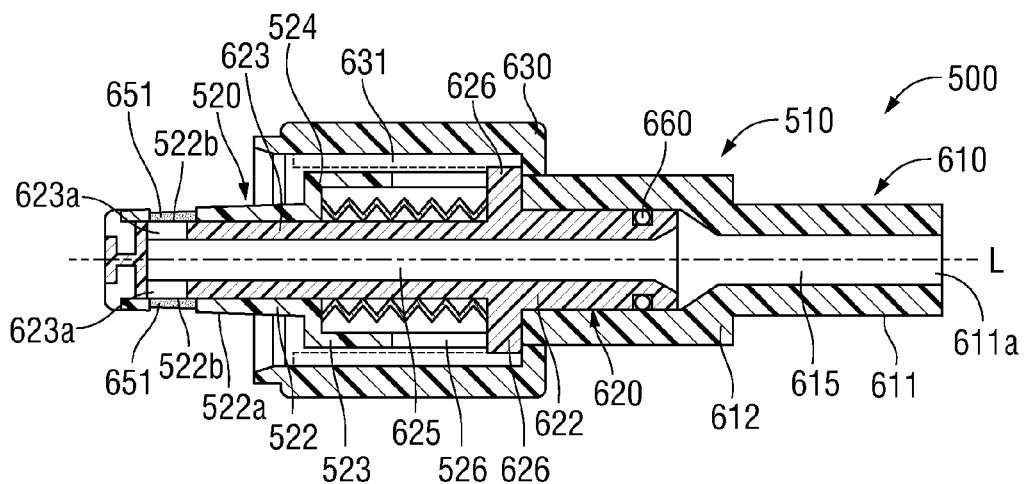
FIG. 15 is a cross section of a male luer connector.

Embodiments of the present invention may include a luer wherein the connection opening part and the conduit part of the main tube are arranged separately and the conduit part is configured to move in a fluid-tight manner relative to the connection opening part. FIG. 15 is a cross section of the major parts of male luer connector (500) in such an embodiment. In the illustrated embodiment, which includes main tube (510) of male luer connector (500), first part (610) and second part (620) are formed separately. First part (610) may be formed with connection opening part (611) and outer insertion part (612). Connection opening part (611) is a portion at which a tube, such as a medical treatment tube, may be connected to first opening (611a) at the right end in the figure. Outer insertion part (612) may be connected and coupled to connection opening part (611) and its inner diameter and outer diameter may be larger than the connection opening part. Therefore, first part (610) may have a stepped, round, tubular shape. A first channel (615) penetrating first part (610) may also be formed inside it from connection opening part (611) to outer insertion part (612).

Second part (620) may include conduit part (623) and inner insertion part (622). Conduit part (623) may have a round, tubular shape. One end surface (the left end surface in FIG. 15) may be closed, and a second opening (623a) may be formed in the outer circumferential surface positioned near that end surface. One or a plurality of second openings (623a) may be formed in the circumferential orientation in conduit part (623). Inner insertion part (622) may be the portion formed at the right side in the figure of conduit part (623) and may have a round, tubular shape. A second channel (625) penetrating from conduit part (623) to inner insertion part (622) may be formed on the inside of second part (620). Projecting parts (626) also may be formed on second part (620) between conduit part (623) and inner insertion part (622). Projecting parts (626) may be formed protruding to the outside diametrally from second part (620). In one embodiment, four projecting parts (626) may be formed at 90 degree intervals in the circumferential direction.

As can be seen from FIG. 15, inner insertion part (622) of second part (620) may be taken in toward the inner circumference of outer insertion part (612) of first part (610). Here, the inner diameter of outer insertion part (612) may be slightly larger than the outer diameter of outer insertion part (622). Therefore, inner insertion part (622) can move axially in the inner circumference of outer insertion part (612). An O-ring (660) may also be attached between the inner wall of outer insertion part (612) and the outer wall of inner insertion part (622). Therefore, when inner insertion part (622) is housed in outer insertion part (612), the first channel (615) inside first part (610) and the second channel (625) inside second part (620) may be connected in a fluid-tight manner by O-ring (660).

Male luer member (520) may have a stepped, round, tubular shape and may be mounted on the outer circumference of conduit part (623) of main tube (510) to cover it. Male luer member (520) may include male side taper part (522) and base part (523). Male side taper part (522) may be a round, tubular portion formed at the left side of male luer member (520) in FIG. 15, and it may have a tapered outer wall (522a), the outer diameter of which decreases going from right to left in FIG. 15, in a similar fashion to that of male side taper part (122) in aforementioned embodiments.

Base part (523) may be formed to the right side in the figure of male side taper part (522). Base part (523) have a round, tubular shape coaxial with male side taper part (522) and its outer diameter may be larger than the outer diameter of male side taper part (522). Therefore, a stepped part (524) that extends radially toward the outside in the circumferential direction may be formed between male side taper part (522) and base part (523). A long narrow slit (526) may also be formed in the axial direction in base part (523). Projecting part (626) of main tube (510) may be taken into slit (526) and interference when male luer member (520) and main tube (510) move axially may be prevented by slit (526).

A third opening (522b) may also be formed in the outer circumference at the left side in the figure of male side taper part (522). Third opening (522b) may be formed facing second opening (623a) formed in the outer circumference of conduit part (623) as shown in the figure. Therefore, second opening (623a) and third opening (522b) may be connected. In addition, a filter (651) may be attached in third opening (522b). Filter (651) may be attached to close third opening (522b) and may have the properties of being gas permeable but impermeable to liquid.

A lock ring (630) may also be attached to cover the outer circumference of male luer member (520) and main tube (510) as shown in FIG. 15. Lock ring (630) exhibits a round, tubular shape, and a threaded part (631) may be formed on the inner circumference. The end surface at the right side of lock ring (630) in FIG. 15 extends inward diametrally as can be seen from the figure and the tip of projecting part (626) that protrudes from slit (526) can engage.

In such an embodiment, during priming, gas, such as air, in first channel (615) and second channel (625) may pass from second opening (623a) to third opening (522b) and confront filter (651). Filter (651) may have outstanding gas permeability, so the gas may be transmitted through filter (651) and discharged outside. In this case, since filter (651) may be impermeable to liquid, the liquid may be prevented from leaking out with discharge of the gas.

Figure 16A:
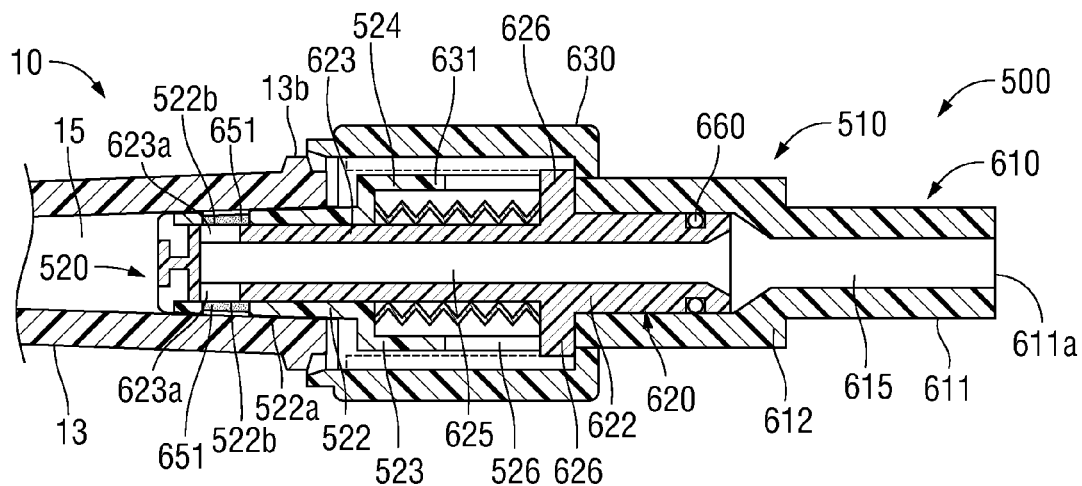
FIG. 16 is a cross section of the male luer connector in FIG. 15 and a female luer connector in various positions with respect to one another as they are being coupled.
Figure 16B:
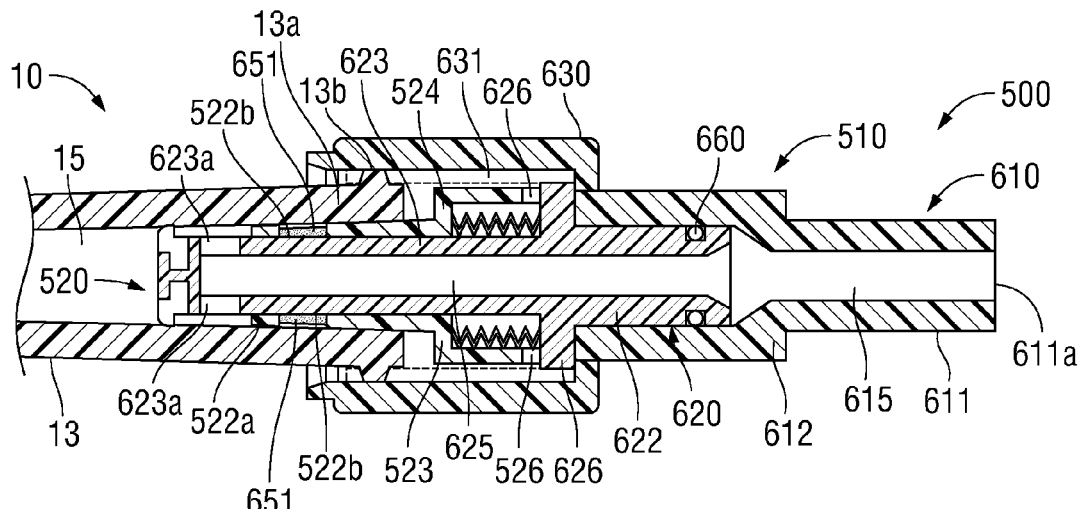

FIG. 16 illustrates coupling male luer connector (500) to female luer connector (10). Specifically, FIG. 16(*a*) shows the two connectors coupled. However, in FIG. 16(*a*) first channel (615) and second channel (625) of male luer connector (500) and channel (15) of female luer connector (10) are not connected. FIG. 16(*b*) shows the two connectors coupled such that first channel (615) and second channel (625), and channel (15) are connected.

As shown in FIG. 16(*a*), female luer connector (10) and male luer connector (500) may be brought into proximity, and tapered inner wall (13a) of female side taper part (13) and tapered outer wall (522a) of male side taper part (522) may be brought into contact. Then, when female luer connector (10) is moved further to the right in FIG. 16, male luer member (520) may move to the right along with female luer connector (10) with the contact between tapered inner wall (13a) and tapered outer wall (522a) maintained. Second opening (623a) that has been closed by filter (651) attached in third opening (522b) of male luer member (520) may be opened by the movement of male luer member (520). Because of this, first channel (615) and second channel (625) may connect to channel (15) in female luer member (10) through second opening (623a). Therefore, liquid in first channel (615) and second channel (625) in main tube (510) may flow out through second opening (623a) and toward female luer connector (10). This may be descriptive of the state shown in FIG. 16(*b*).

Figure 17:
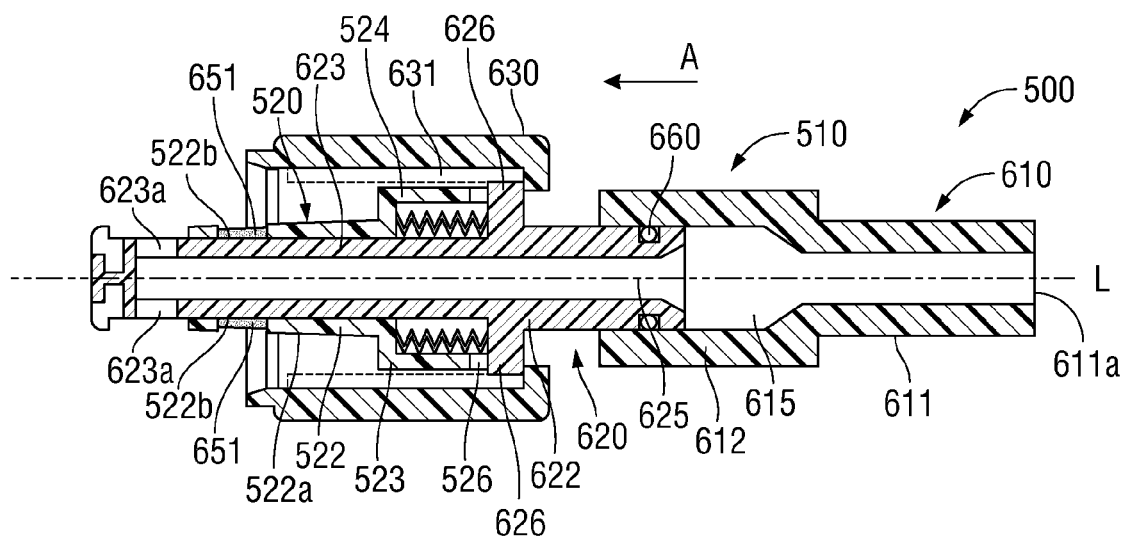
FIG. 17 is a cross section of the male luer connector in FIG. 15 with an actuated lock ring.

Then, bubbles sometimes remain in channels (615) and (625) after priming is completed as explained with respect to aforementioned embodiments. In this case, when channels (615), (625) are already filled with liquid by priming, even if liquid pressure is provided, the bubbles remaining in the channels may not move toward filter (651). Thus, such residual bubbles may resist removal by priming. In this embodiment, should such residual bubbles be present, lock ring (630) may be manually pulled to the left as indicated by arrow (A) as shown in FIG. 17. When lock ring (630) is moved to the left in the figure, projecting part (626) engaged in lock ring (630 may) also move to the left. Projecting part (626) may be formed in second part (620) of main tube (510), so second part (620) may move to the left by movement to the left of lock ring (630).

In this case, since first part (610) and second part (620) of main tube (510) are formed separately, first part (610) may not move and only second part (620) may move. Because projecting part (626) may be disposed to enter slit (526) formed in male luer member (520), when projecting part (626) moves to the left, it moves inside slit (526) and male luer member (520) and projecting part (626) do not interfere with each other. Therefore, lock ring (630) and second part (620) of main tube (510) may move by the operation of moving aforementioned locking ring (630) to the left.

The facing positions of conduit part (623) and male luer member (520) may be displaced axially by the movement of second part (620) and second opening (623a) that has previously been closed by filter (651) attached in third opening (522b) of male luer member (520) may be opened. Because of this, first channel (615) and second channel (625) may connect to the outside through second opening (623a). If liquid pressure is supplied from the medical treatment tube connected to channel opening part (611) in this state, liquid in channels (615) and (625) of main tube (510) may flow out through second opening (623a). Bubbles remaining in channel (615) and (625) may be moved by the liquid flow and discharged outside through second opening (623a). Residual bubbles can be discharged outside by operating lock ring (630) manually in this way.

Operation such as this has essentially the same function and effects as explained with respect to aforementioned embodiments. With this embodiment, a lever part (225) or the like may not be provided, and the assembly may be such that residual bubbles can be removed by operating the lock ring itself. When a lever part (225) is furnished, in order to remove residual bubbles, lock ring (230) may be held with one hand and lever part (225) may be operated with the other hand. In contrast to this, with male luer connector (500) of this embodiment, this operation can be carried out with one hand, for example, by gripping lock ring (630) with one hand and by moving first part (610) in a direction away from lock ring (630) with a finger on the hand gripping lock ring (630). Because of this, operability may be improved.

In this embodiment as above, main tube (510) may be provided with a first part (610) that includes a connection opening part (611) that has a first opening (611a), and a second part (620) that has a second opening (623a) and that also includes a conduit part (623) on which a male luer member (520) may be mounted on the outer circumference. Further, first part (610) and second part (620) may be formed separately. Second part (620) that includes conduit part (623) may also be constituted to be able to move relative to male luer member (520) to close and open second opening (623a) by the operation of lock ring (630). Therefore, when the liquid in channels (615) and (625) is discharged outside to discharge residual bubbles, conduit part (623) may be moved by the operation of lock ring (630) and second opening (623a) can be opened to discharge the liquid inside channels (615) and (625) outside.

Figure 18:
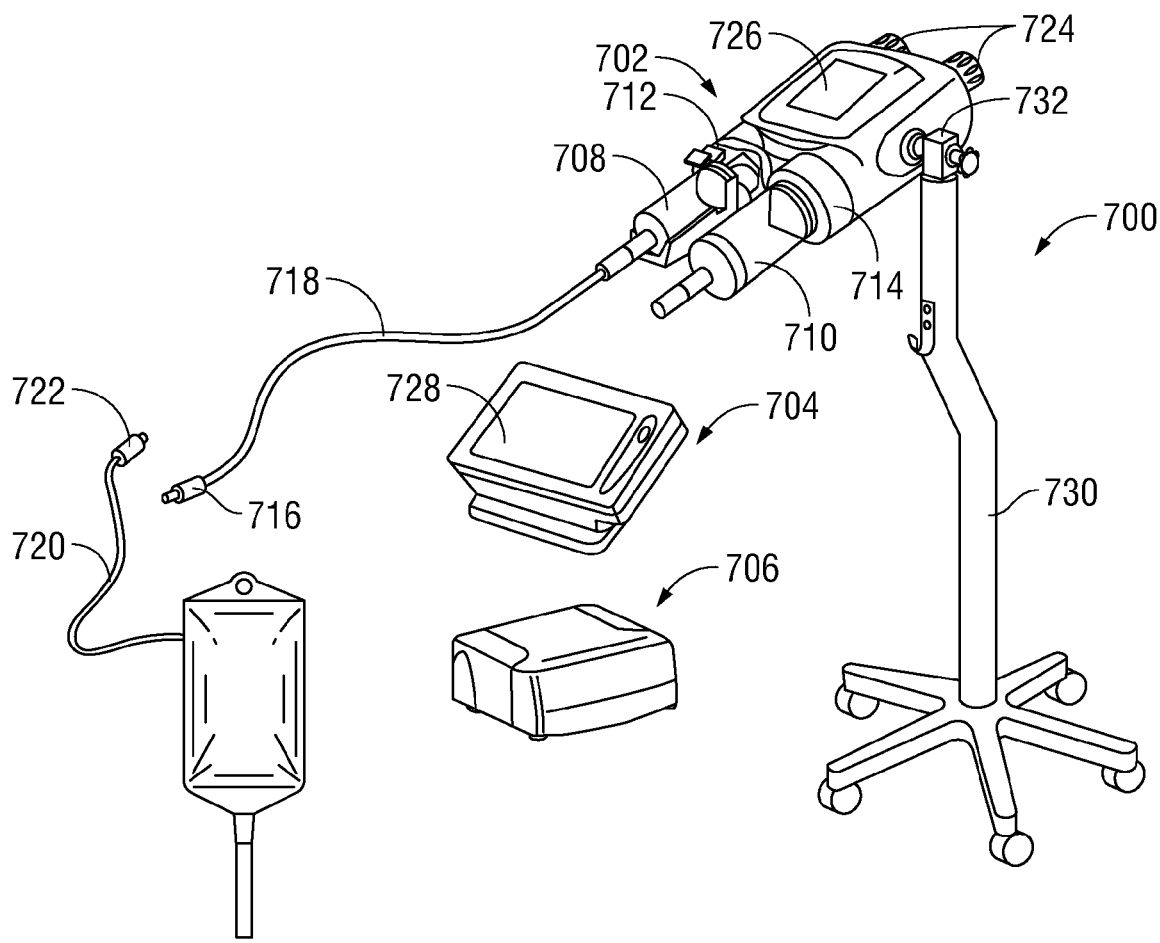
FIG. 18 is a perspective view of a power injector system.

FIG. 18 is a perspective view of a power injector system that incorporates a male luer connector in accordance with present embodiments. The power injector system is generally indicated by reference number (700). In the illustrated embodiment, the power injector system (700) includes various functional components, such as a powerhead (702), a console (704), and a power pack (706). Syringes (708), (710) are mounted to the power injector system (700) in faceplates (712), (714) of the powerhead (702), and various injector controls are used to fill the syringes (708), (710) with medical fluid (e.g., contrast media). The power injector system (700) may then be used to inject the medical fluid into a subject under investigation or a subject being treated using operator or pre-programmed control. In the process of injecting the subject and preparing to inject the subject with the medical fluid, a male luer connector (716) in accordance with present embodiments may be utilized on tubing (718) extending from one or both of the syringes (708), (710). For example, as discussed above, the male luer connector (716) may be in fluid communication with one or both of the syringes (708), (710) and may be utilized to purge gas bubbles from the medical fluid. Further, the male luer connector (716) may be utilized to couple the tubing (718) to tubing (720) that provides access to the patient by coupling the male luer connector (716) to a female luer connector (722) that is coupled to the tubing (720). In some embodiments, the syringes (708), (710) may include the male luer connector (716) on a tip portion, for example, The injector powerhead (702) may include one or more hand-operated knobs (724) for use in controlling the movement of the internal drive motors engaged to syringes (708), (710), and a display (726) for indicating to the operator the current status and operating parameters of the injector. The console (704) may include a touch screen display (728), which may be used by the operator to remotely control operation of the power injector system (700). The display (728) may also be used to specify and store programs for automatic injection, which can later be automatically executed by the power injector system (700) upon initiation by the operator.

The powerhead (702) and the console (704) may connect through cabling (not shown) to the power pack (706). The power pack (706) may include a power supply for the injector, interface circuitry for communicating between the console (704) and powerhead (702), and further circuitry permitting connection of the power injector system (700) to remote units. For example, the remote units may include remote consoles, remote hand or foot control switches, or other original equipment manufacturer (OEM) remote control connections allowing, for example, the operation of power injector system (700) to be synchronized with the x-ray exposure of an imaging system.

The powerhead (702) may be mounted to a wheeled stand (730), which may include a support arm (732) for supporting the powerhead (702) for easy positioning of the powerhead (702) in the vicinity of the examination subject. The console (704) and the power pack (706) may be placed on a table or mounted on an electronics rack in an examination room. In other embodiments, the powerhead (702) may be supported by a ceiling, floor or wall mounted support arm.

The invention claimed is:

1. A male luer connector for coupling medical tubing, comprising:
   a main tube comprising:
      a tube connection opening;
      a vent opening;
      a main tube channel that extends along a first axis from the tube connection opening to the vent opening;
      a filter disposed within the vent opening; and
      a circumferential opening that extends through a wall of the main tube from the main tube channel to an outer side of the wall of the main tube along a second axis that is angled with respect to the first axis; and
   a male luer member disposed about the main tube such that an inner side of a wall of the male luer member is adjacent the outer side, of the wall of the main tube, the male luer member comprising:
      a base opening;
      a tip opening; and
      a male luer member channel that extends along the first axis from the base opening to the tip opening.

2. The connector of claim 1, comprising a lock ring disposed about the male luer member.

3. The connector of claim 2, comprising threads disposed on an inner wall of the lock ring, the threads arranged to face the male luer member.

4. The connector of claim 1, wherein the male luer member comprises a base portion and a tapered portion, the base portion having a larger diameter than the tapered portion and being connected to the tapered portion via a stepped portion.

5. The connector of claim 4, comprising a resilient component that is disposed adjacent the stepped portion and between the outer side of the wall of the main tube and the inner side of the wall of the male luer member.

6. The connector of claim 5, wherein the main tube comprises a coupling portion and a conduit portion, the coupling portion having a larger diameter than the conduit portion.

7. The connector of claim 6, wherein part of the base portion of the male luer member is slidably disposed within the coupling portion of the main tube.

8. The connector of claim 1, wherein an inner diameter of the male luer member increasingly tapers toward the tip opening and an outer diameter of the main tube correspondingly increasingly tapers toward the vent opening.

9. The connector of claim 1, wherein the main tube comprises a coupling portion and a separate conduit portion, the coupling portion being removably coupled to the conduit portion.

10. The connector of claim 1, wherein the filter is gas permeable and substantially impermeable to liquid.

11. An injector system for medical applications, comprising:
    a syringe; and
    a male luer connector of claim 1 in fluid communication with the syringe.

12. The system of claim 11, comprising a powerhead coupled to the syringe, the powerhead configured to actuate the syringe.

13. The system of claim 12, comprising a console configured to facilitate user control of the powerhead.

14. A male luer connector for coupling medical tubing, comprising:
    a main tube comprising:
       a tube connection opening;
       a tip end;
       a main tube channel that extends along a first axis from the tube connection opening to the tip end; and
       a circumferential opening that extends through a wall of the main tube from the channel to an outer side of the wall of the main tube along a second axis that is angled with respect to the first axis;
    a male luer member configured to slide over the main tube between a closed position in which the male luer member covers the circumferential opening and an open position in which the male luer member reveals at least a portion of the circumferential opening; and
    a gas permeable filter that is substantially impermeable to liquid.

15. The connector of claim 14, wherein the male luer member comprises the gas permeable filter.

16. The connector of claim 15, wherein the tip end comprises a vent opening.

17. The connector of claim 16, wherein the gas permeable filter is disposed within the vent opening.

18. The connector of claim 14, wherein the male luer member comprises a resilient material.

19. The connector of claim 14, comprising a manual lever slidably arranged within the male luer connector and extending from the male luer member.

20. The connector of claim 19, wherein the manual lever comprises a slit and a projection from the main tube is disposed within the slit.

21. The connector of claim 14, comprising a resilient component biasingly positioned adjacent the main tube and the male luer member.

22. The connector of claim 21, wherein the resilient component is disposed between the outer side of the wall of the main tube and the inner side of the wall of the male luer member.

23. The connector of claim 21, wherein the resilient component is disposed along an outer wall of the male luer member.

24. The connector of claim 21, wherein the resilient component exhibits a bellows shape.

25. The connector of claim 21, wherein the resilient component comprises a spring.

26. An injector system for medical applications, comprising:
    a syringe; and
    a male luer connector of claim 14 in fluid communication with the syringe.

27. The system of claim 26, comprising a powerhead coupled to the syringe, the powerhead configured to actuate the syringe.

28. The system of claim 27, comprising a console configured to facilitate user control of the powerhead.

29. A male luer connector for coupling medical tubing, comprising:
    a main tube comprising:
        a tube connection opening;
        a tip end;
        a main tube channel that extends along a first axis from the tube connection opening to the tip end; and
        a circumferential opening that extends through a wall of the main tube from the channel to an outer side of the wall of the main tube along a second axis that is angled with respect to the first axis; and
    a male luer member slidably disposed adjacent the main tube such that an inner side of the male luer member is adjacent the outer side of the wall of the main tube and the male luer member covers the circumferential opening when the male luer member is in an extended position, wherein the male luer member includes an elastic material that is gas permeable.

30. An injector system for medical applications, comprising:
    a syringe; and
    a male luer connector of claim 29 in fluid communication with the syringe.

31. The system of claim 30, comprising a powerhead coupled to the syringe, the powerhead configured to actuate the syringe.

32. The system of claim 31, comprising a console configured to facilitate user control of the powerhead.

33. A method of using a male luer connector, the method comprising:
    filling a main tube of the male luer connector with medical fluid;
    purging gas from the main tube through a filter of the male luer connector, wherein the filter resists liquid transport;
    contacting a male luer member of the male luer connector with a female luer member of the female luer connector, wherein the male luer member occludes a hole defined in the main tube at least prior to the contacting;
    moving the male luer member away from the hole using the female luer connector; and
    flowing the medical fluid through the hole from the main tube to the female luer member.

* * * * *